(12) United States Patent
Sung et al.

(10) Patent No.: US 9,791,384 B2
(45) Date of Patent: Oct. 17, 2017

(54) X-RAY IMAGING APPARATUS AND METHOD FOR GENERATING X-RAY IMAGE

(71) Applicant: SAMSUNG ELECTRONICS CO., LTD., Suwon-si (KR)

(72) Inventors: Young Hun Sung, Hwaseong-si (KR); Dong-Goo Kang, Hwaseong-si (KR); Ji Young Choi, Suwon-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 169 days.

(21) Appl. No.: 14/930,811

(22) Filed: Nov. 3, 2015

(65) Prior Publication Data

US 2016/0209336 A1 Jul. 21, 2016

(30) Foreign Application Priority Data

Jan. 21, 2015 (KR) .................. 10-2015-0009675

(51) Int. Cl.
*G01N 23/04* (2006.01)
(52) U.S. Cl.
CPC ....... *G01N 23/04* (2013.01); *G01N 2223/401* (2013.01); *G01N 2223/423* (2013.01)
(58) Field of Classification Search
CPC ........ G01N 23/00; G01N 23/02; G01N 23/04; G01N 23/043; G01N 23/08; G01N 23/083; G01N 2223/401; G01N 2223/423; A61B 6/482; A61B 6/485; A61B 6/504; A61B 6/4035; H04N 5/32; H04N 5/321; G06T 5/50; G06T 2207/10116; G06T 2207/10121; G06T 2207/10124

USPC ....... 378/42, 62, 98.8, 98.9, 98.12; 382/128, 382/132

See application file for complete search history.

(56) References Cited

U.S. PATENT DOCUMENTS

| | | | |
|---|---|---|---|
| 2008/0025588 A1 | 1/2008 | Zhang et al. | |
| 2010/0128955 A1 | 5/2010 | Walimbe et al. | |
| 2015/0139394 A1* | 5/2015 | Kang | A61B 6/5211 378/62 |
| 2015/0363939 A1* | 12/2015 | Choi | A61B 6/5264 382/132 |

FOREIGN PATENT DOCUMENTS

JP 2010-500901 A 1/2010

* cited by examiner

*Primary Examiner* — Jurie Yun
(74) *Attorney, Agent, or Firm* — Sughrue Mion, PLLC

(57) ABSTRACT

An X-ray imaging apparatus and a method for generating X-ray images are provided. The X-ray imaging apparatus includes an X-ray source configured to irradiate X-rays to a subject, and an X-ray detector configured to detect X-rays penetrating the subject, and generate a frame image including pieces of X-ray data for energy bands. The X-ray imaging apparatus further includes an image divider configured to divide the frame image into images of substances, using the pieces of the X-ray data, and an image generator configured to restore the frame image by performing motion compensation on an image of a first substance of the frame image, among the images of the substances of the frame image, and an image of the first substance of a previous frame image.

29 Claims, 18 Drawing Sheets

X-RAY IMAGING APPARATUS AND METHOD FOR GENERATING X-RAY IMAGE

CROSS-REFERENCE TO RELATED APPLICATION

This application claims priority from Korean Patent Application No. 10-2015-0009675, filed on Jan. 21, 2015, in the Korean Intellectual Property Office, the disclosure of which is incorporated herein by reference in its entirety.

BACKGROUND

1. Field

Apparatuses and methods consistent with exemplary embodiments relate to an X-ray imaging apparatus and a method for generating an X-ray image.

2. Description of the Related Art

X-ray imaging apparatuses are devices for obtaining an image of an internal part of a subject by irradiating X-rays to the subject and using X-rays that penetrates the subject. Because X-ray transmittance varies depending on characteristics of the substances that make up the subject, images of an internal structure of the subject may be captured using intensity or strength of the X-rays that penetrate the subject.

X-ray video technologies allowing observation of movements inside the subject have been developed and applied in intervention treatment such as angiography or X-ray diagnosis such as X-ray fluoroscopy.

SUMMARY

Exemplary embodiments may address at least the above problems and/or disadvantages and other disadvantages not described above. Also, the exemplary embodiments are not required to overcome the disadvantages described above, and an exemplary embodiment may not overcome any of the problems described above.

One or more exemplary embodiments include an X-ray imaging apparatus and a method for generating X-ray images, by which a high resolution image may be obtained even with low dose X-ray irradiation.

According to an aspect of an exemplary embodiment, an X-ray imaging apparatus includes an X-ray imaging apparatus including an X-ray source configured to irradiate X-rays to a subject, and an X-ray detector configured to detect X-rays penetrating the subject, and generate a frame image including pieces of X-ray data for energy bands. The X-ray imaging apparatus further includes an image divider configured to divide the frame image into images of substances, using the pieces of the X-ray data, and an image generator configured to restore the frame image by performing motion compensation on an image of a first substance of the frame image, among the images of the substances of the frame image, and an image of the first substance of a previous frame image.

The image generator may be configured to restore the frame image by combining the motion-compensated images of the first substance, and combining the combined images of the first substance with images of a second substance that are combined among the substances.

The image generator may be configured to perform motion estimation and motion compensation on the image of the first substance of the frame image and the image of the first substance of the previous frame image.

The image divider may be configured to separate the images of the substances from the pieces of the X-ray data, using a difference in an attenuation property between the substances.

The X-ray source may be configured to irradiate X-rays having the energy bands to the subject.

The X-ray source may be configured to irradiate X-rays having each of the energy bands to the subject.

The X-ray source may be further configured to vary energy bands of the irradiated X-rays by changing at least one among a tube voltage and a filter.

The X-ray imaging apparatus may further include a filtering portion configured to filter the irradiated X-rays such that a dose of the X-rays irradiated to a background region of the subject is lower than a dose of the X-rays irradiated to a region of interest of the subject.

The X-ray detector may be configured to detect X-rays penetrating the background region, generate a frame image of the background region including pieces of X-ray data of the background region for multiple energy bands, detect X-rays penetrating the region of interest, and generate a frame image of the region of interest.

The image divider may be configured to divide the frame image of the background region into images of substances, using the pieces of the X-ray data of the background region, and the image generator may be configured to restore the frame image of the background region by performing motion compensation on an image of the first substance of the frame image of the background region, among the images of the substances of the frame image of the background region, and an image of the first substance of a previous frame image of the background region, and restore the frame image of the region of interest by performing high resolution image restoration on the frame image of the region of interest.

The image generator may be configured to combine the restored frame images of the background region and the region of interest into a frame image of the subject.

The X-ray imaging apparatus may further include a color mapper configured to map different color channels to the images of the substances.

According to an aspect of another exemplary embodiment, an X-ray imaging apparatus includes an image divider configured to divide a frame image into images of substances, and an image generator configured to restore the frame image by performing motion compensation on an image of a first substance of the frame image, among the images of the substances of the frame image, and an image of the first substance of a previous frame image.

The image divider may be configured to divide a frame image of a background region of the subject into images of substances, and the image generator may be configured to restore the frame image of the background region by performing motion compensation on an image of the first substance of the frame image of the background region, among the images of the substances of the frame image of the background region, and an image of the first substance of a previous frame image of the background region, and restore a frame image of a region of interest of the subject by performing high resolution image restoration on the frame image of the region of interest.

According to an aspect of another exemplary embodiment, there is provided a method of generating X-ray images, the method including irradiating X-rays to a subject, detecting X-rays penetrating the subject, and generating a frame image including pieces of X-ray data for energy bands. The method further includes dividing the frame image into images of substances, using the pieces of the X-ray data, and restoring the frame image by performing motion compensation on an image of a first substance of the frame image, among the images of the substances of the frame image, and an image of the first substance of a previous frame image.

The restoring may include combining the motion-compensated images of the first substance, and combining the combined images of the first substance with images of a second substance that are combined among the substances.

The restoring may include performing motion estimation and motion compensation on the image of the first substance of the frame image and the image of the first substance of the previous frame image.

The dividing may include separating the images of the substances from the pieces of the X-ray data, using a difference in an attenuation property between the substances.

The irradiating may include irradiating X-rays having the energy bands to the subject.

The irradiating may include irradiating X-rays having each of the energy bands to the subject.

The generating may include detecting X-rays penetrating a background region of the subject, generating a frame image of the background region including pieces of X-ray data of the background region for multiple energy bands, detecting X-rays penetrating a region of interest of the subject, and generating a frame image of the region of interest.

The dividing may include dividing the frame image of the background region into images of substances, using the pieces of the X-ray data of the background region, and the restoring may include restoring the frame image of the background region by performing motion compensation on an image of the first substance of the frame image of the background region, among the images of the substances of the frame image of the background region, and an image of the first substance of a previous frame image of the background region, and restoring the frame image of the region of interest by performing high resolution image restoration on the frame image of the region of interest.

The restoring may include combining the restored frame images of the background region and the region of interest into a frame image of the subject.

The method may further include determining whether an X-ray imaging apparatus is operating in a low dose mode, and the generating may include generating the frame image including the pieces of the X-ray data for the energy bands, in response to the determining that the X-ray imaging apparatus is operating in the low dose mode.

The method may further include determining whether a mode to restore a frame image through separation of images of substances is selected, and the generating may include generating the frame image including the pieces of the X-ray data for the energy bands, in response to the determining that the mode to restore a frame image is selected.

According to an aspect of another exemplary embodiment, an X-ray imaging apparatus includes an image divider configured to divide a previous frame image into a first previous image of a first body part and a second previous image of a second body part, and divide a current frame image into a first current image of the first body part and a second current image of the second body part. The X-ray imaging apparatus further includes an image generator configured to perform motion estimation and motion compensation on each of the first previous image, the second previous image, the first current image, and the second current image, combine the motion-estimated and motion-compensated first previous image and first current image, combine the motion-estimated and motion-compensated second previous image and second current image, and combine the combined first previous image and first current image with the combined second previous image and second current image to generate the current frame image.

BRIEF DESCRIPTION OF THE DRAWINGS

The above and/or other aspects will become more apparent by describing exemplary embodiments with reference to the accompanying drawings, in which.

DETAILED DESCRIPTION

Figure 1:
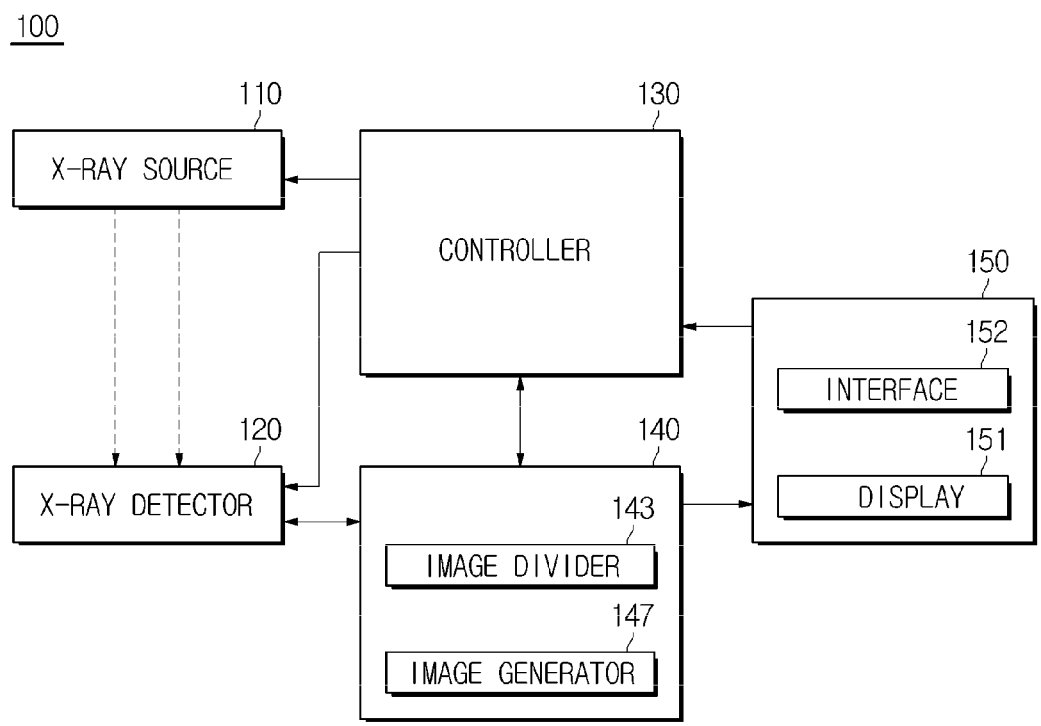
FIG. 1 is a control block diagram of an X-ray imaging apparatus, according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments may be practiced without those defined matters. Also, well-known functions or constructions are not described in detail because they would obscure the description with unnecessary detail.

Figure 2:
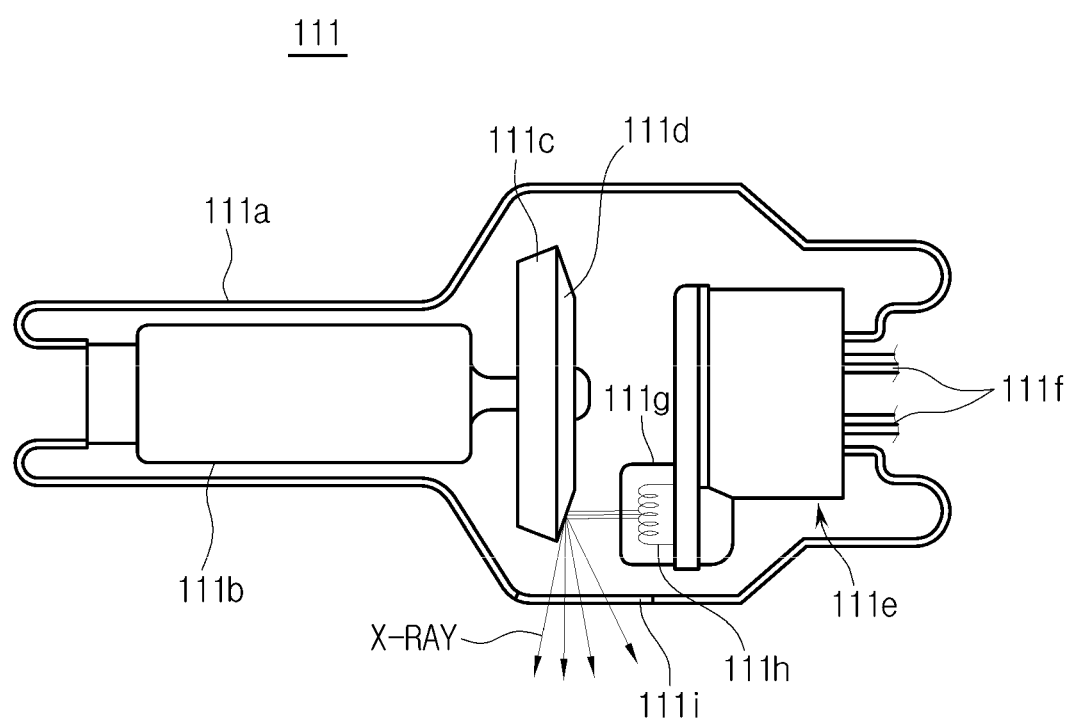
FIG. 2 is a cross-sectional view illustrating an internal structure of an X-ray tube included in an X-ray imaging apparatus, according to an exemplary embodiment.

FIG. 1 is a control block diagram of an X-ray imaging apparatus, according to an exemplary embodiment, and FIG. 2 is a cross-sectional view illustrating an internal structure of an X-ray tube included in the X-ray imaging apparatus, according to an exemplary embodiment.

Referring to FIG. 1, an X-ray imaging apparatus 100 includes an X-ray source 110 for generating and irradiating X-rays, an X-ray detector 120 for detecting irradiated X-rays to obtain frame images, and a controller 130 for controlling operation of the X-ray source 110 and the X-ray detector 120. The X-ray imaging apparatus 100 further includes an image processor 140 for performing image processing on the frame images obtained from the X-ray detector 120, and a user interface 150 for providing information to a user and receiving control commands from the user.

Referring to FIG. 2, the X-ray source 110 includes an X-ray tube 111 for generating X-rays. The X-ray tube 111 is implemented as a bipolar vacuum tube that includes positive and negative electrodes 111c and 111e, and the body of the vacuum tube is a glass tube 111a made of e.g., hard silicon glass. The negative electrode 111e includes a filament 111h and a focusing electrode 111g for focusing electrons. When the inside of the glass tube 111a of the X-ray tube 111 is under a high vacuum, and the filament 111h is heated as current is applied to an electric wire 111f connected to the filament 111h, thermoelectrons (or called 'thermions') are produced. However, the negative electrode 111e is not limited to have the filament 111h, and a carbon nano-tube that may be driven with high-rate pulses may also be used for the negative electrode 111e.

The positive electrode 111c is mainly made of copper, and a target material 111d is applied or disposed on the side that faces the negative electrode 111e, the target material including a high resistive material, such as Cr, Fe, Co, Ni, W, Mo, or the like. The higher the melting point of the target material is, the smaller the focal spot size is.

When a high voltage is applied across the positive and negative electrodes 111c and 111e, the thermions produced from the filament 111h collide with the target material of the positive electrode 111c, which produces X-rays. The X-rays are irradiated out through a window 111i that may use a thin film of Beryllium (Be). The target material 111d is rotated by a rotor 111b. While the target material 111d is rotating, heat build-up rate may increase more than ten times per unit area as compared with an occasion where the target material 111d is stationary, and the focal spot size may decrease.

The voltage applied across the positive and negative electrodes 111c and 111e is called a tube voltage, the magnitude of which may be represented in kilovolt peak (kvp). As the tube voltage increases, the speed of the thermion increases, and as a result, energy of X-radiation (energy of photon radiation) produced from collision of the thermion with the target material increases. Moreover, a filter may be arranged in the direction of X-ray irradiation to control the X-ray energy. With the filter arranged on the front or back side of the window, the X-rays of the energy band may be filtered. For example, when a filter of aluminum or copper is arranged, X-rays of a low energy band are filtered out, and thus the energy of the irradiated X-rays increases. Current flowing through the X-ray tube is called a tube current, which may be represented by an average value mA. As the tube current increases, a dose of X-rays (the number of photons of X-rays) also increases. Accordingly, the energy of X-radiation may be controlled by at least one of the tube voltage or the filter, and the dose of X-rays may be controlled by the tube current and time for being exposed to X-radiation.

Referring again to FIG. 1, the X-ray imaging apparatus 100 may generate X-ray video clips, which may be used in many different fields of diagnosis or associated treatment fields, such as X-ray fluoroscopy or angiography. The X-ray video clip may be generated in real time and displayed on a display 151. The X-ray imaging apparatus 100 may perform successive X-ray scans to generate an X-ray video clip. As a scheme of performing successive X-ray scans, there may be a continuous exposure scheme and a pulse exposure scheme.

In a case that the continuous exposure scheme is employed, a low tube current is continuously applied to the X-ray tube to produce continuous X-rays, while in a case that the pulse exposure scheme is employed, short pulses of tube voltage is applied to the X-ray tube to produce the X-rays in the form of pulses. Any of the two schemes may be employed in exemplary embodiments of the present disclosure.

The X-ray source 110 may irradiate X-rays into an area of the subject (subject area) multiple times at predetermined or arbitrary time intervals. The predetermined or arbitrary time interval may be determined based on pulse rates or frame rates, and the pulse rate may be determined based on the frame rate, and vice versa. The frame rate may be set to 30 frames per second (fps), 15 fps, 7.5 fps, etc. For example, if the frame rate is set to 15 fps, the pulse rate is set to 15 pulses per second (pps) and accordingly, X-rays may be produced 15 times in a second.

The subject refers to an object subject to an X-ray scan, i.e., an object, the inside of which is to be represented by an X-ray image, and the subject area refers to a region that includes the subject and is to be captured into an X-ray image. Accordingly, the subject area may correspond to or include a field of view (FOV) of the X-ray imaging apparatus 100. The subject area includes a region of interest and a background region. The subject area exclusive of the region of interest corresponds to the background region. Accordingly, if the location of the region of interest is known, the location of the background region may be known as well. The region of interest may be a region including an object of interest. The object of interest is an object that has constant attention during X-ray scanning, including a treatment instrument used for the subject, or a region for treatment or a part of lesions. For example, in a case the X-ray imaging apparatus 100 is used in angiography, a treatment instrument, such as a guide wire, catheter, needle, balloon, stent, etc., is closely observed while it is being inserted into a blood vessel. In this case, the treatment tool may be set up as the object of interest, and information about the treatment tool may be stored in advance. In the case that a region for treatment or a part of lesions is set up to be an object of interest, a region having stenosis, aneurysm, cancerous region, or the like, may be the object of interest.

The X-ray detector 120 may detect X-rays to obtain multiple frame images of the subject area. The frame image refers to each of multiple X-ray images obtained at a frame rate of the X-ray imaging apparatus 100. The X-ray detector 120 may have a two dimensional (2D) array structure of a plurality of pixels, and may generate an X-ray image of the subject area by converting detected X-rays to electric signals for each pixel.

The X-ray detector 120 may be classified by the method for converting detected X-rays to electric signals and/or method for obtaining X-ray data.

First, the X-ray detector 120 may be classified by the method for converting X-rays to electric signals to have a direct conversion scheme or indirect conversion scheme. In the direct conversion scheme, when X-rays are irradiated, pairs of electron and hole are generated temporarily inside the photo detector and electric potential applied across both electrodes of the photo detector causes the electrons to be moved to the positive electrode and the holes to be moved to the negative electrode. The X-ray detector 120 then converts the movements into an electric signal. In the direct conversion scheme, the material used for the photo detector may be e.g., a-Se, CdZnTe, HgI2, PbI2, etc. In the indirect conversion scheme, there is a scintillator between the photo detector and the X-ray generator.

The scintillator reacts with the X-rays irradiated from the X-ray generator and emits photons with wavelengths in the visible-ray region. The photo detector detects the photons emitted from the scintillator and converts them to an electric signal. The material used for the photo detector in the indirect conversion scheme may be e.g., a-Si, and the scintillator may be GADOX scintillator in the form of a thin film, or a micro column type or needle structure type CSI (T1).

Furthermore, the X-ray detector 120 may be classified by how to obtain X-ray data into charge integration mode in which a signal is obtained from charges that have been stored for a predetermined time and photon counting mode in which photons with energy levels higher than a threshold energy level are counted each time a signal is generated from a single X-ray photon.

Once X-rays are irradiated from the X-ray source 110 and frame images are obtained from the X-rays that penetrate the subject at a frame rate set by the X-ray detector 120, the display 151 may provide an X-ray video clip of the subject by displaying the frame images.

As described above, for capturing an X-ray video clip, the X-ray imaging apparatus 100 obtains X-ray images that amount to a few to tens of frames per second. At this time, the subject, e.g., a portion of a patient body, keeps being exposed to X-radiation. Because a treatment using the X-ray video clip has a time duration from a few minutes for short up to more than one hour, a method for reducing the patient's exposure to the X-radiation is used.

To reduce the X-ray dose to which the patient is exposed, a lower dose of X-rays may be irradiated. However, frame images obtained from such low dose X-ray irradiation usually have lower signal to noise ratios (SNRs) and thus have lower resolution. This problem may be solved in a way that increases the SNR of the current frame image to be displayed on the display 151 by combining it with previous multiple frame images obtained from lower dose X-ray irradiation (multi-frame restoration). In this case, if the subject makes a motion, the motion may cause image blurring to the combined image, thereby blurring the combined image.

To avoid the image blurring by compensating for an impact of the motion of the subject, a motion estimation and compensation scheme may be applied between frame images. Unlike an ordinary image that only shows the surface of an object, an X-ray image is captured by X-ray penetration of many tissues, and thus motion properties appear to overlap in many different tissue images. Accordingly, if an ordinary motion compensation scheme is employed, even a motionless tissue may actually be compensated, which causes distortion of an X-ray image obtained by combining frame images with motion compensation applied. The present disclosure provides a method to address the problem that may arise in a situation where the subject tends to move a lot and a low dose of X-rays are to be irradiated. In other words, the present disclosure provides a method to increase the resolution of an X-ray video clip by increasing SNRs of frame images while obtaining the X-ray video clip through low dose X-ray irradiation to reduce the subject's exposure to the X-radiation.

The X-ray imaging apparatus 100 in accordance with the present disclosure may obtain frame images by irradiating a low dose of X-rays with multiple energy bands, dividing the frame images each into multiple X-ray images for multiple energy bands, and performing motion compensation. How to obtain frame images with low dose X-ray irradiation with the multiple energy bands will now be described in detail, and how to divide the multiple frame images by substances having different motion properties will then be described.

Once X-rays are irradiated to the subject from the X-ray source 100, attenuation levels of the X-rays may vary depending on the types of substances inside the subject and/or the energy bands of the irradiated X-rays. The extent to which the X-rays attenuate may be represented in numerical values called attenuation coefficients. The attenuation coefficient may vary by the substances inside the subject.

Figure 3:
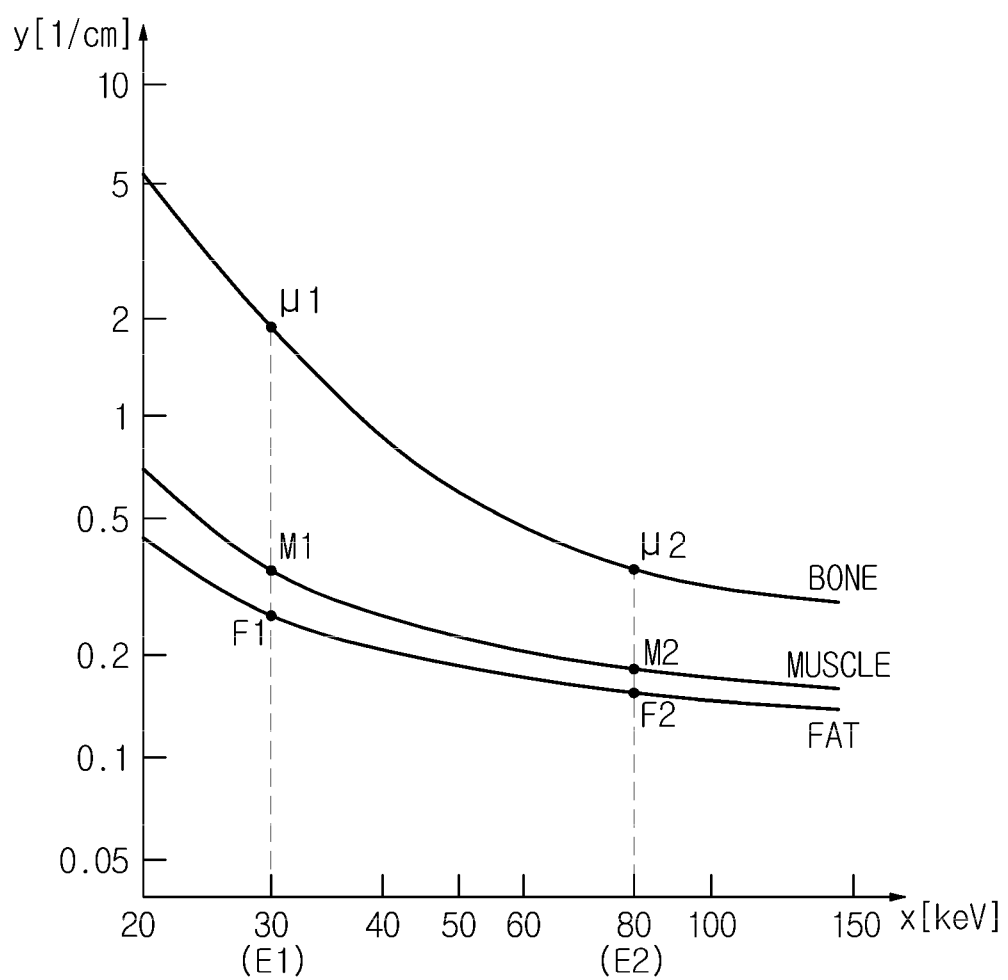
FIG. 3 is a graph representing relationships between energy and attenuation coefficients for respective substances inside a subject.

FIG. 3 is a graph representing relationships between energy and attenuation coefficients for respective substances inside a subject. The x-axis represents energy of photons irradiated to the subject, and the y-axis represents attenuation coefficients. Referring to FIG. 3, a curve representing the attenuation coefficient of the bones is located above a curve representing the attenuation coefficient of soft tissues (muscle, fat). When X-rays with the same energy band, e.g., $E_1$ are irradiated, the attenuation coefficient of the bones ($\mu_1$) is greater than that of the muscle ($M_1$), which is greater than that of the fat ($F_1$). In other words, different substances inside the subject have different attenuation coefficients, and the higher the atom number or the density is, and/or the harder the substance is, the more the attenuation coefficient increases. The attenuation coefficient may vary by energy bands of the irradiated X-rays. In the graph of FIG. 3, when X-rays with energy bands $E_1$ and $E_2$ are irradiated to the bones, a substance of the subject, the attenuation coefficient $\mu_1$ for the lower energy band $E_1$ is greater than the attenuation coefficient $\mu_2$ for the higher energy band $E_2$. Even in the case that the substance of the subject is a muscle or fat, it may be seen that the attenuation coefficient $M_1$ or $F_1$ in X-ray irradiation with the lower energy band $E_1$ is greater than that $M_2$ or $F_2$ in X-ray irradiation with the higher energy band $E_2$. In other words, the lower the energy band of the X-rays irradiated to the subject is, the more the attenuation coefficient increases. Such attenuation coefficients may be represented in the following equation 1:

$$I = I_0 \cdot e^{-\mu(E) \cdot T} \quad (1)$$

where $I_0$ refers to an intensity of X-rays irradiated to a substance, I refers to an intensity of X-rays that has penetrated the substance, and $\mu(E)$ refers to an attenuation coefficient of the substance for the X-rays with energy E. T refers to a thickness of the substance through which the X-rays passes.

According to the equation 1, it may be seen that the more the attenuation coefficient increases (i.e., the harder the substance is or the lower the energy band of the irradiated X-rays is) and the thicker the substance is, the lower the intensity of the X-rays that has penetrated is.

As represented in the graph of FIG. 3, as the attenuation coefficient of the substance varies by energy levels, X-ray images with different energy bands are obtained, and images of separate substances may be obtained from the X-ray images with different energy bands, using the attenuation property per substance in respective energy bands.

Figure 4A:
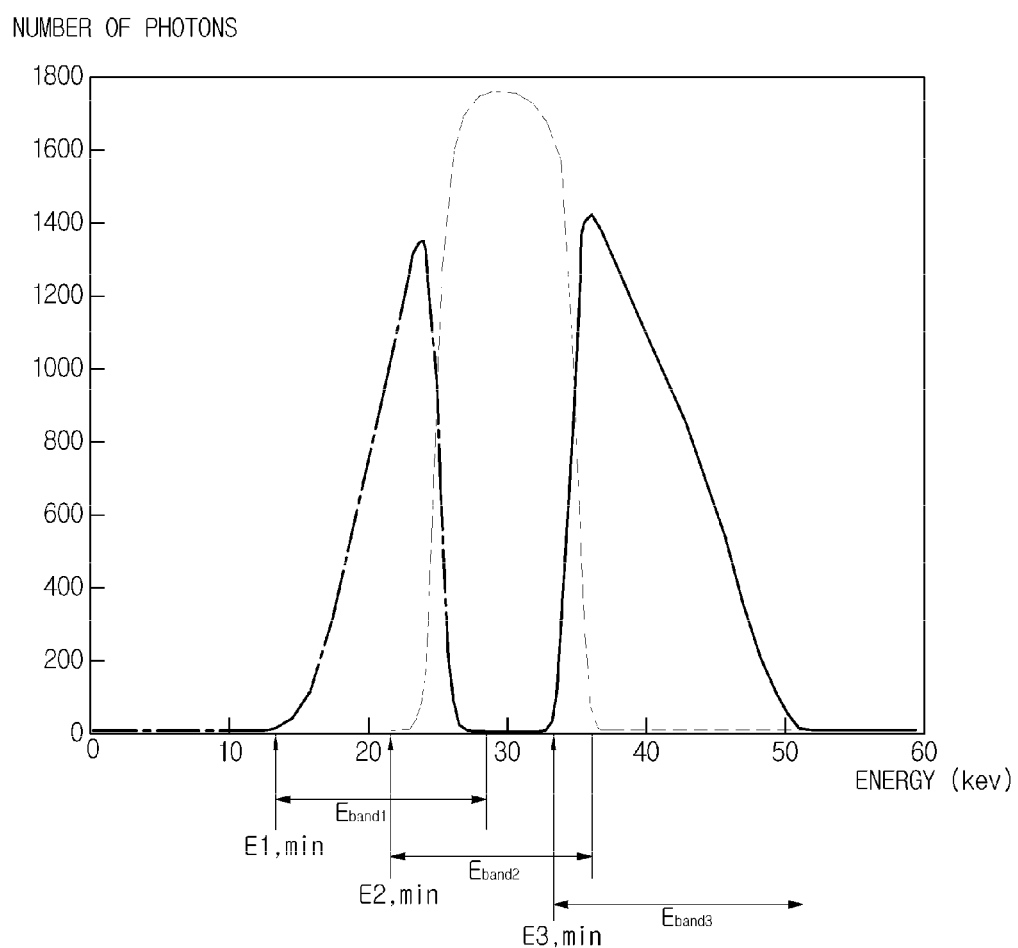
FIG. 4A is a graph representing an X-ray spectrum divided into different energy bands.

For example, to obtain separated images of three substances, X-ray images for different energy bands $E_{band1}$, $E_{band2}$, $E_{band3}$ may be obtained, as shown in FIG. 4A.

Figure 4B:
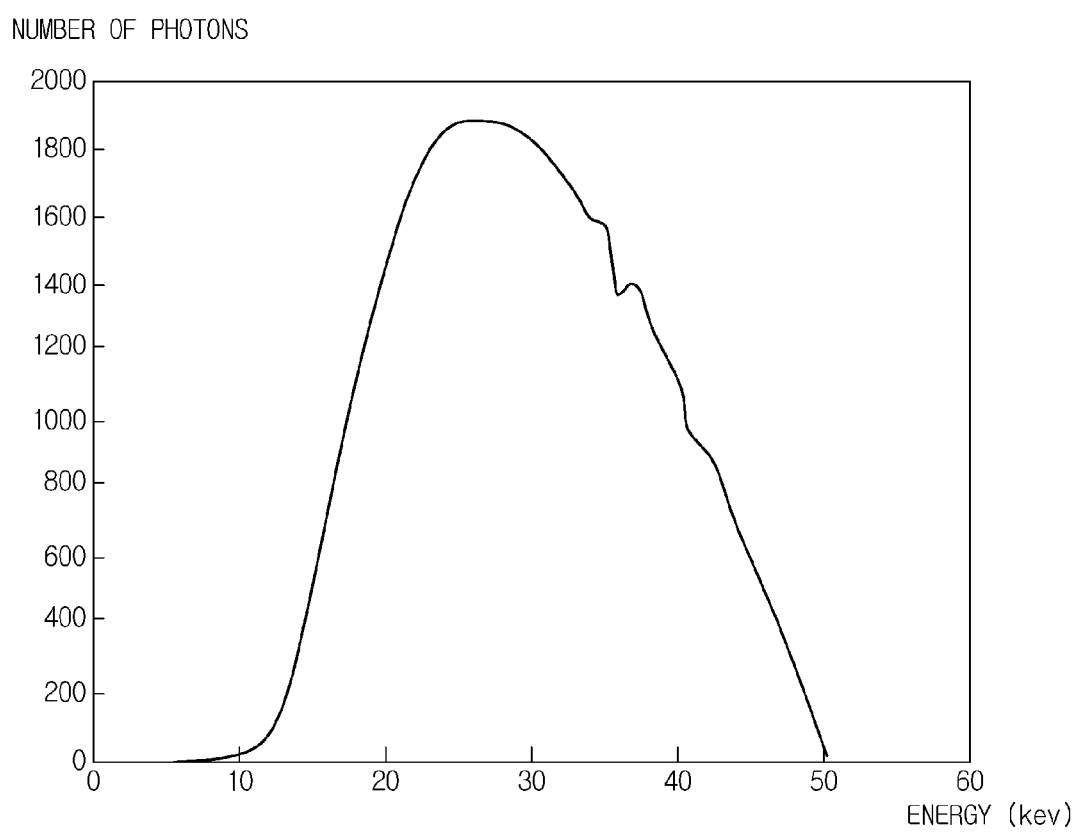
FIG. 4B is a graph representing a spectrum of X-rays irradiated from an X-ray source.

FIG. 4A is a graph representing an X-ray spectrum divided into different energy bands, and FIG. 4B is a graph representing a spectrum of X-rays irradiated from an X-ray source. For convenience of explanation, it is illustrated that the vertical axes of FIGS. 4A and 4B represent the number of photons, but they may be substituted with intensity of X-rays. As a way of obtaining X-ray images in different energy bands, there are a method for irradiating X-rays multiple times while varying the energy band, by the X-ray source, and a method for irradiating a wide band of X-rays at once, by the X-ray source, and detecting and dividing them into different energy bands, by the X-ray detector. If the former method is employed by the X-ray imaging apparatus, the X-ray source irradiates X-rays of $E_{band1}$, and the X-ray detector detects them to obtain an X-ray image for the energy band $E_{band1}$. With the same method, X-ray images for $E_{band2}$ and $E_{band3}$ are obtained as well. If the latter method is employed by the X-ray imaging apparatus, the X-ray source irradiates a wide band of X-rays at once, including three energy bands, as shown in FIG. 4B, and the X-ray detector detects and divides the X-rays into respective energy bands.

As shown in FIG. 4B, for example, X-rays of an energy range from lower limit of 10 keV to higher limit of 50 KeV may be generated and irradiated. For this, the X-rays may be generated at 50 kvp of tube voltage, and irradiated after a lower energy band, about 0 to 10 kev, is filtered out. A dose of X-rays (the number of photons) represented on the y-axis may be controlled by the tube current and X-ray exposure time.

To divide the detected X-rays by energy bands, the X-ray detector may be implemented in a photon counting method.

Figure 5:
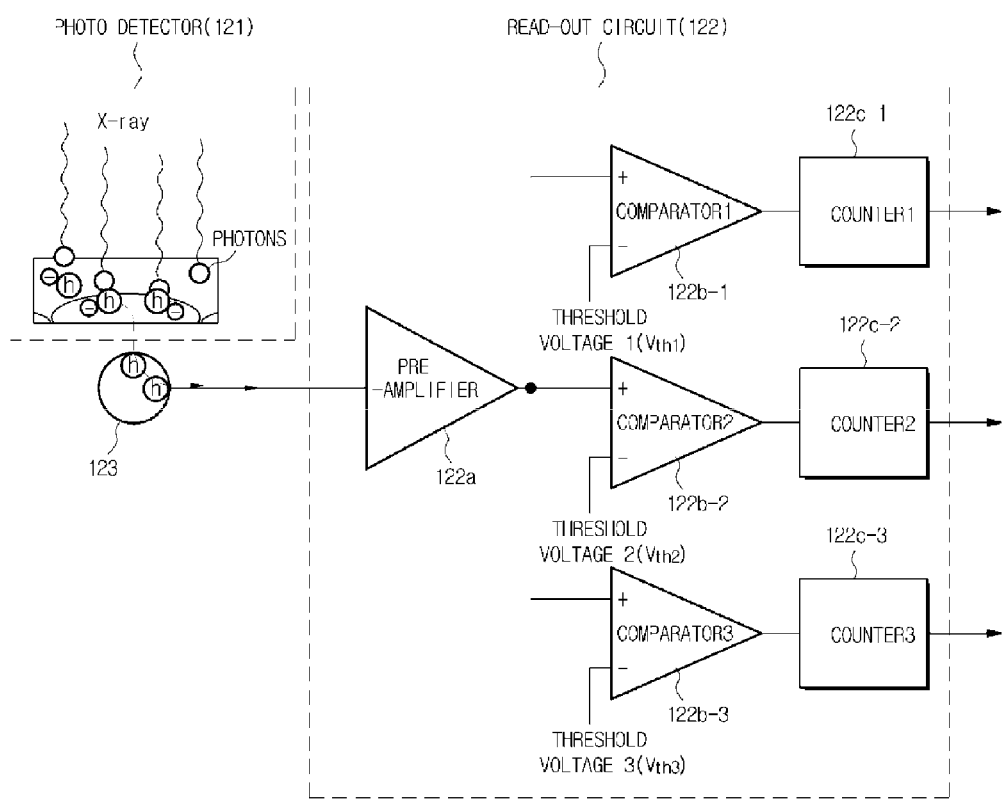
FIG. 5 is a single pixel structure of a photon counting X-ray detector.

FIG. 5 is a diagram illustrating a single pixel structure of a photon counting X-ray detector. Referring to FIG. 5, when photons of the X-rays are incident on a photo detector 121, energy of the photons is delivered to electrons that have been in the valence band and the electrons are thus excited beyond the band gap energy difference into the conduction band. This produces electron-hole pairs in the depletion region. When a metal electrode is formed on the photo detector 121 and reverse biased, electrons of the electron-hole pairs generated in the depletion region are drawn into the n-type region while holes are drawn into the p-type region.

When the holes drawn into the p-type region are input to a read-out circuit 122 through bump bonding 123, the read-out circuit 122 may read an electric signal generated from the photons. However, it is also possible that the electric signal is generated when electrons are input to the read-out circuit 122 according to the structure of the photo detector 121 and the applied voltage. The read-out circuit 122 may have a 2D pixel array structure, and an electric signal is read out from each pixel.

When charges are input to the read-out circuit 122 from the photo detector 121 through the bump bonding 123, a pre-amplifier 122a of the read-out circuit 122 integrates input charges produced from a single photon and outputs a corresponding voltage signal. The voltage signal output from the pre-amplifier 122a is then input to a comparator 122b. The comparator 122b compares the input voltage signal with a threshold voltage controllable from outside, and outputs a pulse signal having 1 and 0 levels according to the comparison result.

A counter 122c outputs digital X-ray data by counting level '1's from the pulse signal. An X-ray video clip may be obtained by combining X-ray data per pixel. The threshold voltage corresponds to the threshold energy, and in a case of counting the number of photons with energy levels equal to or greater than energy E, a threshold voltage corresponding to the threshold energy E may be input to the comparator 122b. The reason for corresponding the threshold energy to the threshold voltage is that the level of the electric signal (voltage) generated from the photo detector 121 varies by photon energy. Accordingly, relation between the photon energy and corresponding voltage is used to calculate a threshold voltage corresponding to a threshold energy. Hereinafter, inputting threshold energy to the X-ray detector may be interpreted as inputting a threshold voltage corresponding to the threshold energy. To divide the detected X-rays into multiple energy bands, there may be multiple comparators. Although three comparators 122b-1, 122b-2, 122b-3 are illustrated in FIG. 5, the X-ray detector is not limited thereto, but may have fewer or more comparators depending on the number of energy bands for division.

Once electrons or holes produced by a single photon are input to the pre-amplifier 122a through the bump bonding 123 and output as a voltage signal, the voltage signal is input to the three comparators 122b-1, 122b-2, 122b-3. With respective threshold voltages $V_{th1}$, $V_{th2}$, $V_{th3}$ input to the comparators 122b-1, 122b-2, 122b-3, the comparator 1 122b-1 compares an input voltage with the threshold voltage $V_{th1}$ and a counter 1 122c-1 counts the number of photons that generates voltages greater than the threshold voltage 1 $V_{th1}$. In the same way, a counter 2 122c-2 may count the number of photons that generate voltages greater than the threshold voltage 2 $V_{th2}$, and a counter 3 122c-3 may count the number of photons that generate voltages greater than the threshold voltage 3 $V_{th3}$. The number of photons for each energy band, which has been counted by the X-ray detector, may be input to the image processor as digital X-ray data. In an exemplary embodiment, as described above, the X-ray detector may input respective X-ray data for the multiple energy bands, e.g., three energy bands $E_{band1}$, $E_{band2}$, $E_{band3}$ for each frame to an image divider 143 of FIG. 1. In other words, a frame image obtained by the X-ray detector at a frame rate and input to the image divider 143 may include multiple pieces of X-ray data that correspond to the multiple energy bands.

The image divider 143 may separate substance images from the multiple frame images input from the X-ray detector. In an exemplary embodiment, if two types of substances are to be separated, the image divider 143 may separate images of the two substances by performing two-stage operations: applying a weight to at least one of two pieces of X-ray data corresponding to the two energy bands included in the frame image and subtracting them. This is also called dual-energy X-ray absorptiometry.

For example, if the substances to be separated are bones and soft tissues, a weight is applied to X-ray data for a low energy band (hereinafter, referred to as low energy data), and then the result is subtracted from data for a high energy band (high energy data), thus obtaining an image of the soft tissues. In other words, an image from which the bones are eliminated but in which the soft tissues are clearly seen may be obtained. On the contrary, an image of the bones may be obtained by applying a weight to the high energy data and subtracting the result from the low energy data. In other words, an image from which the soft tissues are eliminated but in which the bones are clearly seen may be obtained. It is also possible to obtain an image of the soft tissues or an image of the bones by applying proper weights to the respective low energy data and high energy data and performing subtraction. In this way, the image divider 143 may divide each frame image into two substances, such as bones and soft tissues having different motion properties, thereby generating multiple substance images.

In another example, if there are three or more types of substances for separation, the image divider 143 may separate image of the three or more types of substances from a frame image by applying proper weights to respective pieces of X-ray data that correspond to three energy bands of the frame image and subtracting them. For example, the image divider 143 may divide each frame image into three substances, such as bones, soft tissues, and blood vessels having different motion properties, thereby generating multiple substance images. In exemplary embodiments of the X-ray imaging apparatus, there is no limitations on the number or type of substances for separation. The X-ray apparatus may just obtain a frame image that includes pieces of X-ray data corresponding to a number of substances to be separated and separate the substance images from the frame image using the attenuation property per substance. The method for separating a substance image through weight application and subtraction is only one of examples available to the image divider 143, and there may be many other methods to be used for substance image separation.

Figure 6:
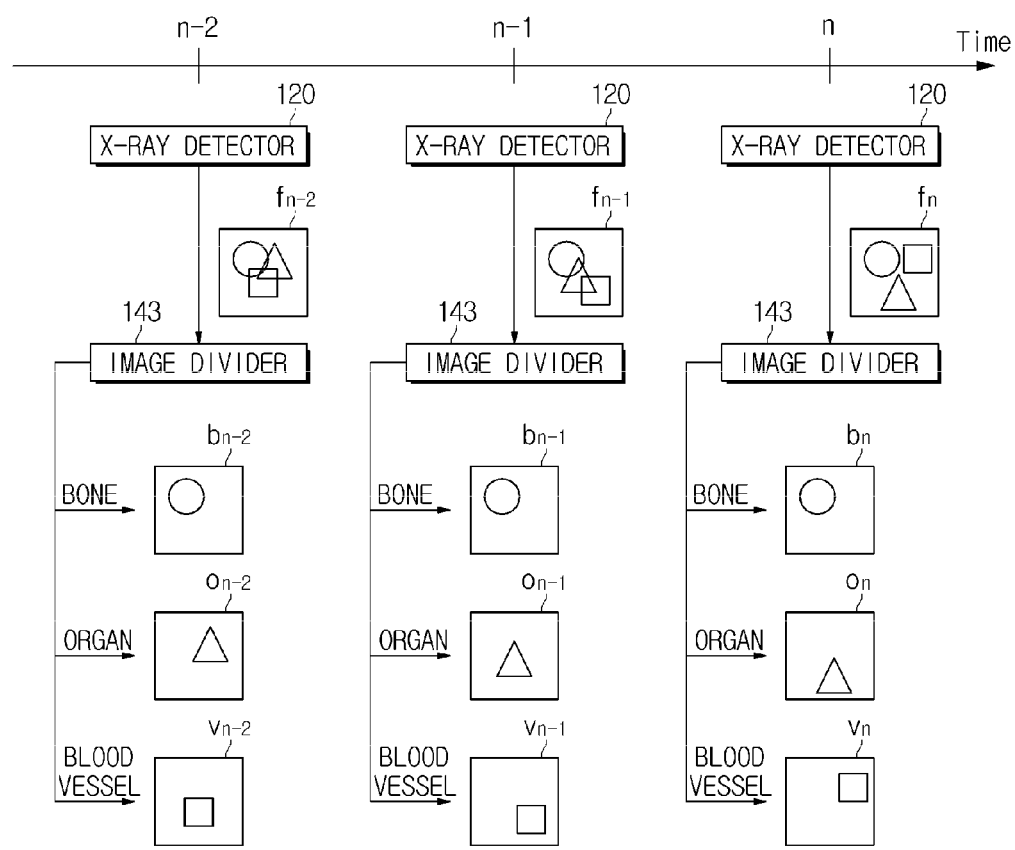
FIG. 6 is a diagram illustrating a conceptual substance separation performed by an X-ray imaging apparatus, according to an exemplary embodiment.

FIG. 6 is a diagram illustrating substance separation performed by an X-ray imaging apparatus, according to an exemplary embodiment. Referring to FIG. 6, the image divider 143 divides each frame image fn−2, fn−1, fn input from the X-ray detector 120 into multiple substance images at each frame n−2, n−1, n. For example, the image divider 143 may divide each of the n−2$^{th}$, n−1$^{th}$, and n$^{th}$ frame images into a bones image, an organ image, and a blood vessel image. Such division of a frame image is to divide each frame image into images that reflect different motion properties. Although each frame image appears to be divided not by motion properties but by types of organs in FIG. 6, division by different organs corresponds to division by motion properties because different organs show different motion properties. For example, bones are said to have little or no motion, soft tissues, such as organs show periodic motions, and blood vessels show rather random motions. Therefore, division of a frame image into different substance images may also reflect different motion properties. Because there may be an occasion where separated substance images do not correspond to motion properties to be separated, information about energy bands corresponding to motion properties to be separated may be stored in advance and used for separation of motion properties.

As shown in FIG. 6, after the image divider 143 divides each of multiple frame images into different substance images, an image generator 147 of FIG. 1 may restore the frame image with an increased SNR through motion estimation and compensation on the separated substance images. Restoration of a frame image by the image generator 147 will now be described in more detail.

Figure 7:
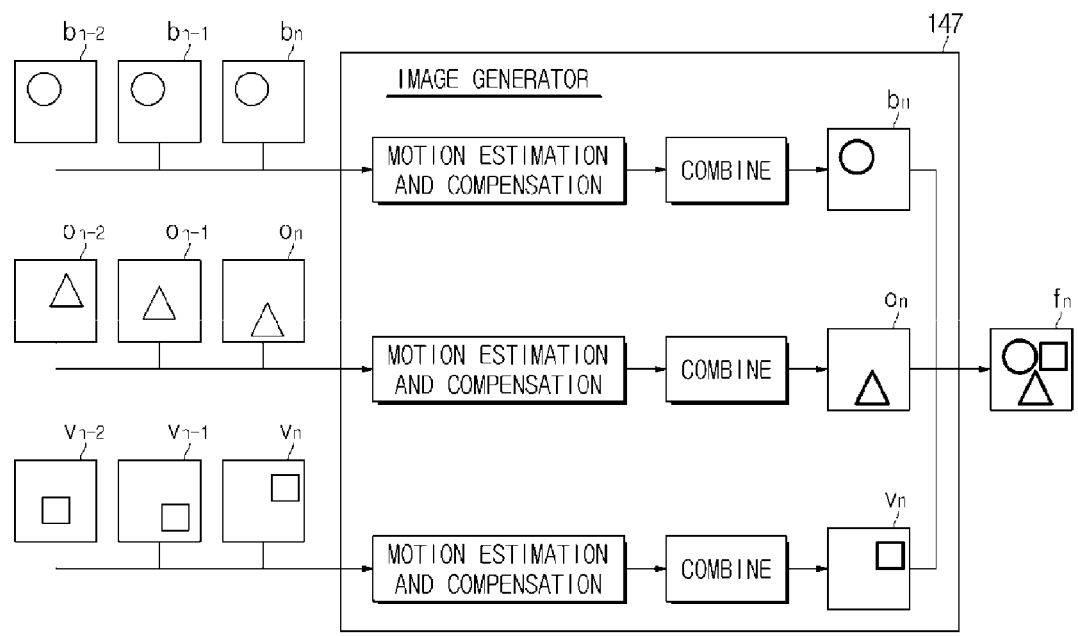
FIG. 7 is a diagram illustrating a conceptual frame image restoration from substance images, performed by an image generator of an X-ray imaging apparatus, according to an exemplary embodiment.

FIG. 7 is a diagram illustrating conceptual frame image restoration from substance images, performed by an image generator of an X-ray imaging apparatus, according to an exemplary embodiment. First, the image generator 147 may increase the SNR by combining images that represent the same substance among the multiple substance images separated from the respective frame images, as shown in FIG. 7.

For example, the image generator 147 may restore a bones image with an increased SNR in the current frame, by combining the bones image of the current frame bn with the same bones images of previous frames bn−2, bn−1, . . . . As for organs or blood vessels, their images may be restored with increased SNRs in the same way. As an example of how to combine a substance image of a current frame with the same substance images of previous frames, there is a method for combining the substance image of the current frame with the substance image of at least one previous frame, or a method for averaging the substance image of the current frame and the substance image of at least one previous frame. Combining as herein used may refer to combining or weight-combining, and averaging may refer to averaging or weight-averaging.

Figure 8:
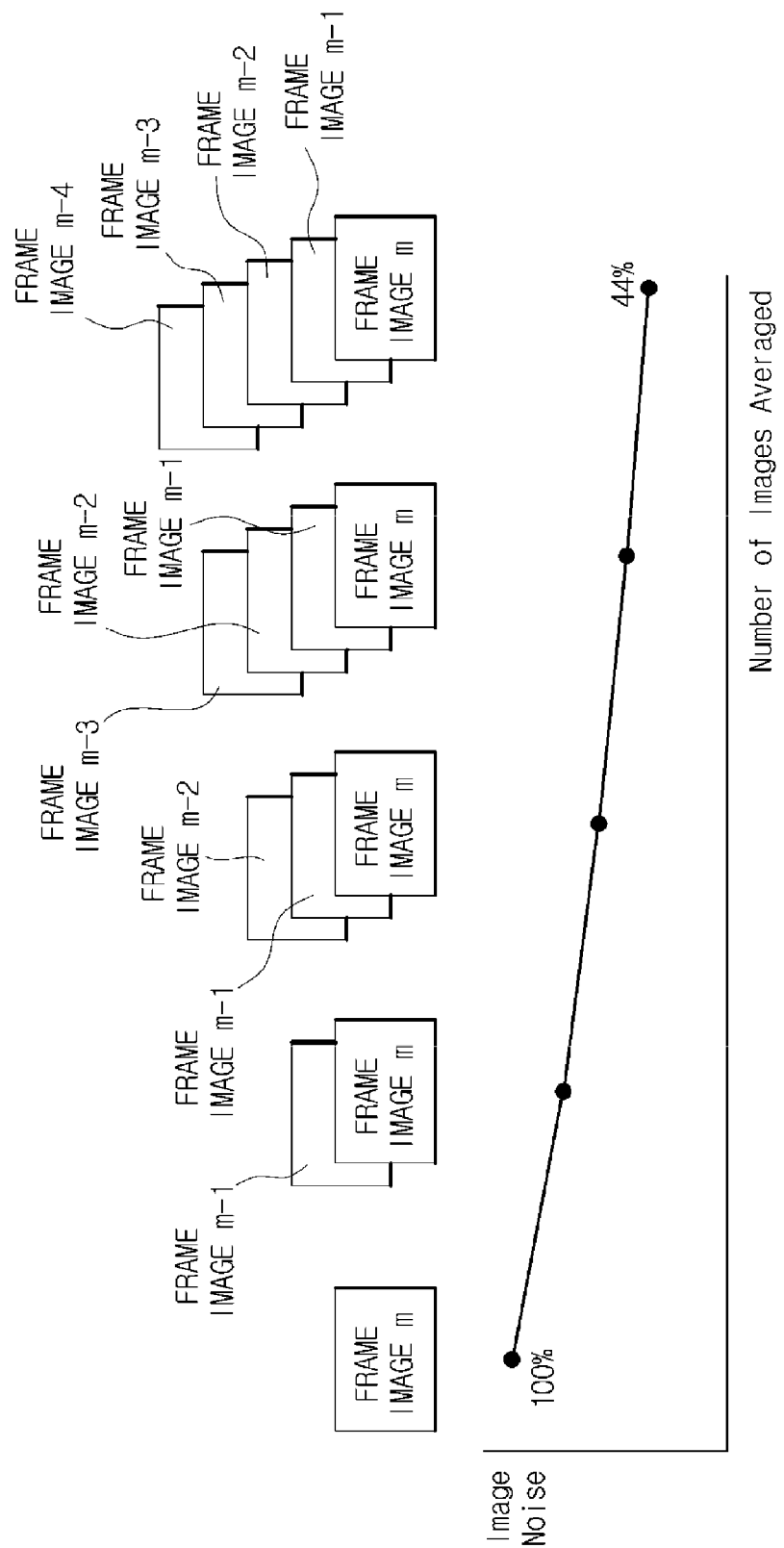
FIG. 8 is a diagram illustrating an effect of reducing noise of a frame image by averaging with previous frame images, according to an exemplary embodiment.

FIG. 8 is a diagram illustrating an effect of reducing noise of a frame image by averaging with previous frame images, according to an exemplary embodiment. Referring to FIG. 8, assuming that a substance image of a current frame is a frame image m, the frame image m may be restored by averaging the frame image m and frame image m−1, or by averaging the frame image m and many previous frame images. As the number of previous frame images increases, the noise reduction rate in the image increases as well. For example, averaging the current frame image m and the previous four frame images may reduce the noise by up to about 60%. The image generator may determine the number of substance images of the previous frames to be used in averaging, taking into account the noise of the substance image of the current frame or image lag.

Figure 9:
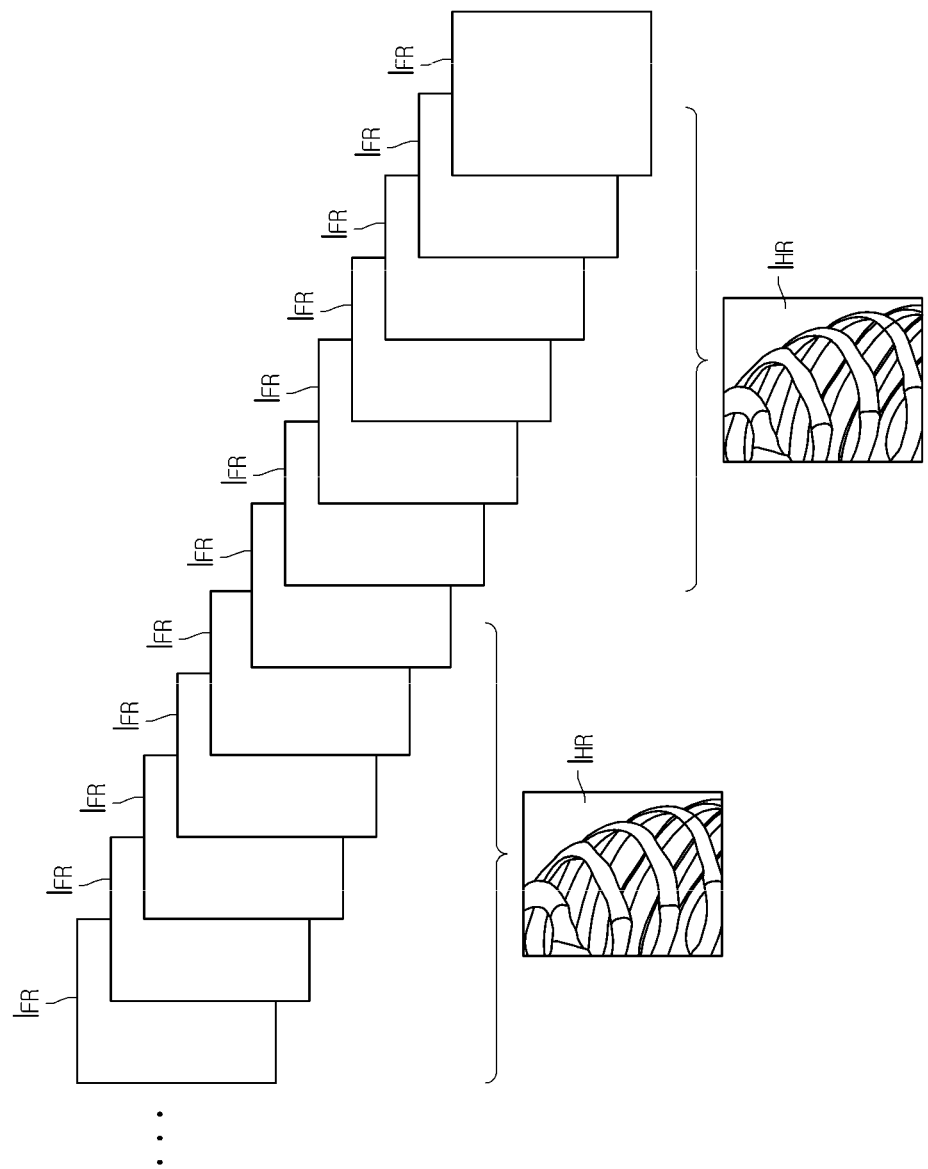
FIGS. 9 and 10 are diagrams illustrating how to combine frame images, according to exemplary embodiments.
Figure 10:
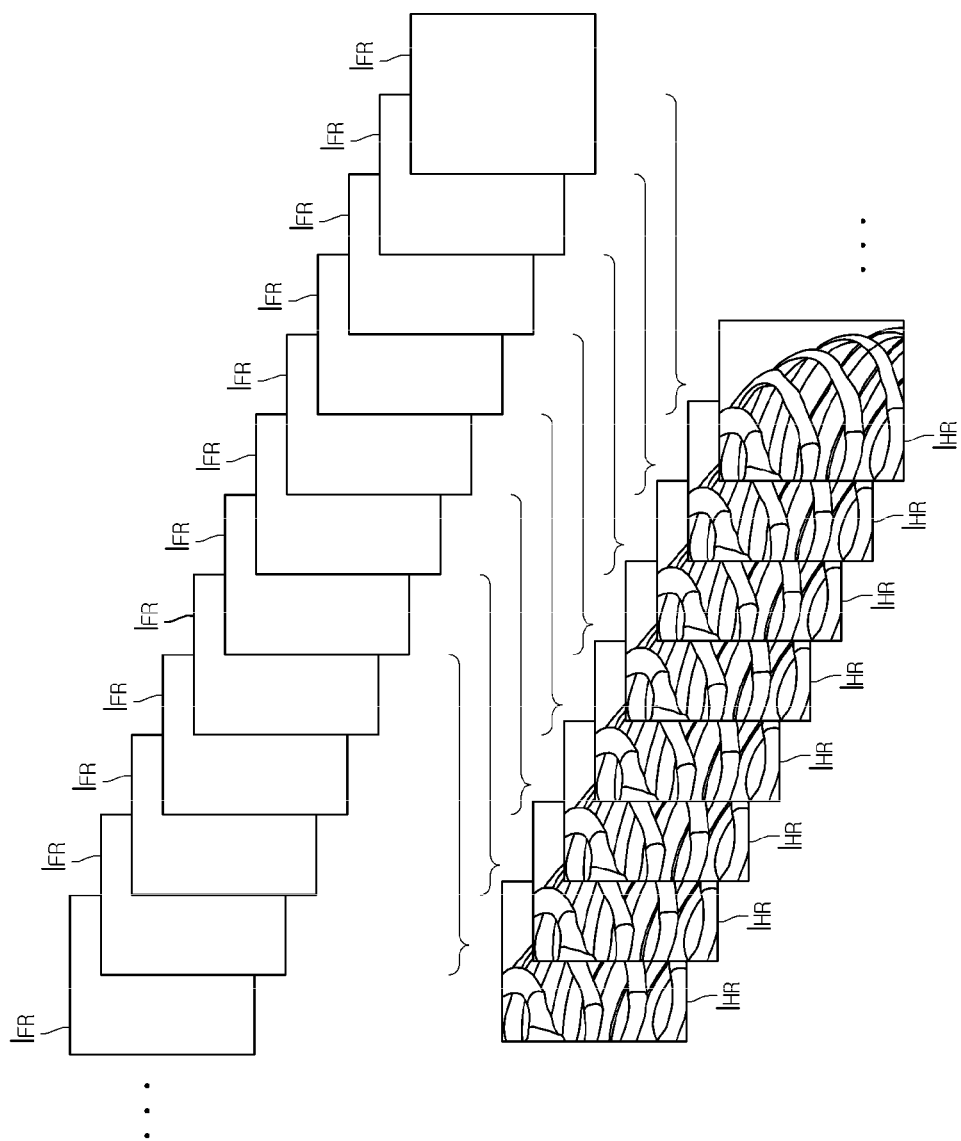

FIGS. 9 and 10 are diagrams illustrating how to combine frame images, according to exemplary embodiments. Referring to FIG. 9, the image generator may perform image restoration each time a predetermined number of images are received. For example, it may perform image restoration each time 6 substance images $I_{FR}$ are received. The image generator may wait until all the six substance images are received, match them to restore a substance image $I_{HR}$ with a good SNR, wait for another six of substance images to be received, and then restore a substance image with a good SNR.

Referring to FIG. 10, the image generator may perform image restoration while shifting substance images one by one, using a sliding window method, instead of waiting until six substance images are received as shown in FIG. 9. There are no limitations on the number of substance images used in the image restoration, although six substance images are used to restore the substance image $I_{HR}$ with a good SNR. As described above, SNR may be improved by combining a substance image of the current frame and substance images of the previous frames, but if there is a motion of the subject between frames, image blurring may occur. Because the X-ray imaging apparatus irradiates a low dose of X-rays, image blurring may be conspicuous due to the motion of a subject if many frames are used for image matching. In an exemplary embodiment, to reduce image blurring that may occur when a substance image of the current frame is combined with substance images of the previous frames as shown in FIG. 7, image enhancement, such as motion estimation and compensation may be performed between substance images in each frame. As a motion field model for motion estimation/compensation, translational motion, block-based piecewise translation motion, rotation, scaling, non-rigid deformable motion, etc., may be used.

The image generator may restore a substance image having a good SNR by combining a substance image of the current frame with the same substance images of the previous frames, and in the restoration process, motion estimation and compensation may be applied to avoid image blurring due to motion of the subject. The image generator may finally restore the current frame image by combining respective substance images in the current frame with enhanced SNR and image blurring. The frame image restored in the low-dose image restoration scheme has excellent SNR and resolution even though it has been obtained with low-dose X-ray irradiation. Accordingly, the X-ray imaging apparatus may reduce exposure of the subject to X-radiation, and provide the user with an X-ray video clip with high resolution.

The frame image with better SNR, which is restored according to the aforementioned exemplary embodiment, may be displayed on the display with different substances in the frame image coming in different colors via color mapping.

Figure 11:
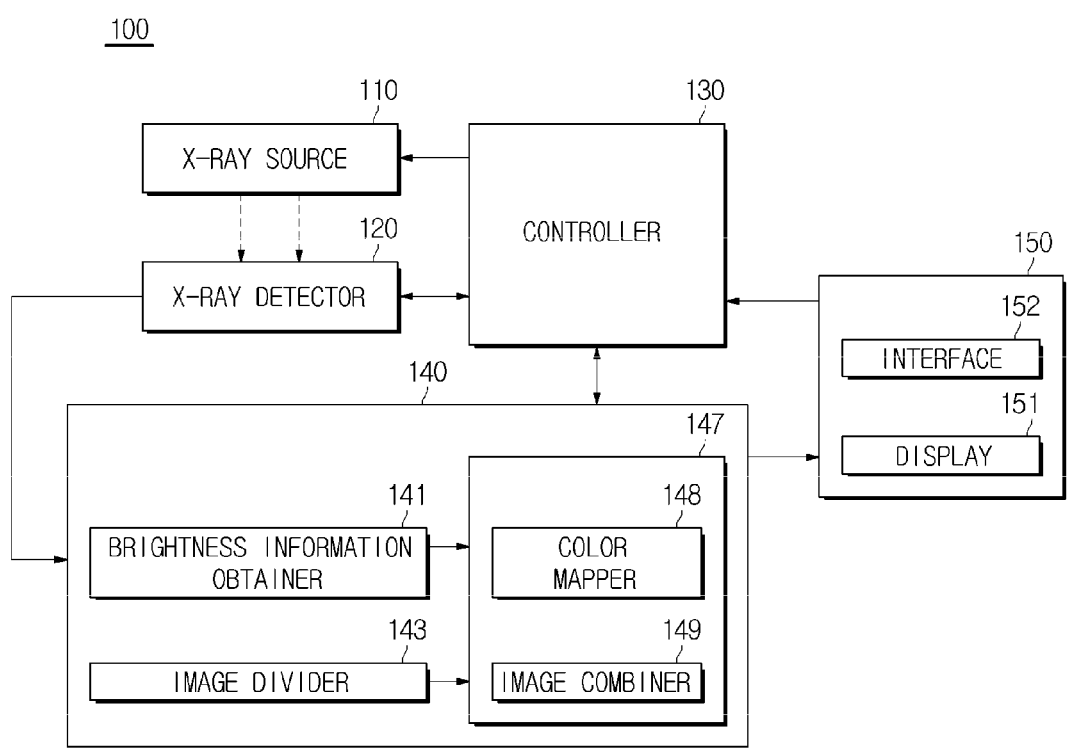
FIG. 11 is a control block diagram of an X-ray imaging apparatus, according to another exemplary embodiment.

FIG. 11 is a control block diagram of an X-ray imaging apparatus, according to another exemplary embodiment. This embodiment is the same as what is described above, so only the configuration associated with the color mapping will now be described.

Referring to FIG. 11, the image processor 140 includes the image divider 143 for separating substance images from a frame image sent from the X-ray detector 120, a brightness information obtainer 141 for obtaining brightness information from the frame image sent from the X-ray detector 120, the image divider 143, and the image generator 147 for generating a final image by applying the brightness information obtained by the brightness information obtainer 141 while mapping different color channels to the separated substance images and combining them.

The image divider 143 is the same as in the aforementioned exemplary embodiment, so the description of the image divider 143 will be omitted herein.

The brightness information obtainer 141 may obtain brightness information from the frame images sent from the X-ray detector 120, to be applied to the final image generated by the image generator 147. The brightness information obtainer 141 may select one of the frame images, and bring brightness information from the selected original frame image as it is, bring brightness information from an average image obtained by averaging the frame images, or bring brightness information from a weight-combined image obtained by weight-combining the frame images. Because all of the original frame image, the average image, and the weight-combined image are black-and-white images, which represent brightness information as they are, the brightness information may imply the corresponding image itself.

A color mapper 148 of the image generator 147 may map the respective substance images separated by the image divider 143 to different color channels. For example, if the image divider 143 separates two kinds of substance images, image 1 and image 2, the image 1 is mapped to a color channel 1 and the image 2 is mapped to a color channel 2. If the image divider 143 separates three kinds of substance images, image 1, image 2, and image 3, the images 1, 2, and 3 are mapped to color channels 1, 2, and 3, respectively.

An image combiner 149 of the image generator 147 may then obtain an image by combining multiple substance images mapped to different color channels and applying thereto the brightness information obtained from the brightness information obtainer 141. In other words, the image combiner 149 may combine the color channels mapped to the respective substance images and brightness information obtained from the brightness information obtainer 141 or a brightness channel mapped to a brightness image into the single image. Operation of the color mapper 148 and image combiner 149 will now be described in more detail.

The color mapper 148 may map color channels, using various color spaces. For example, various color spaces, such as the YUV color space in which color information and brightness information are separated, the Hue Saturation Intensity (HSI) color space, the Hue Saturation Value (HSV) color space, the Cyan Magenta Yellow (CMY) color space in which brightness information is contained in color information, the Cyan Magenta Yellow blacK (CMYK) color space, and Red Green Blue (RGB) color space, etc., may be used by the color mapper 148. An example of using the YUV color space will now be described. The YUV color space represents images using brightness information (Y) and color information (U, V). The color information (U, V) may be representatively expressed in chrominance blue Cb and chrominance red Cr, where Cb is a color difference value of blue and Cr is a color difference value of red. If the image divider 143 separates two substance images, the color mapper 148 may map the substance images 1 and 2 to the Cb and Cr channels, respectively.

The image combiner 149 may then map the Y channel that represents brightness information to a brightness image obtained by the brightness information obtainer 141, and combine the result with the substance images 1 and 2 mapped to the Cb and Cr channels, respectively, thereby generating a single image with discriminative substances because substances 1 and 2 are finally mapped to different colors.

The HSI color space represents an image with hue, saturation, and intensity. Accordingly, the color mapper 148 maps different colors to the respective substance images, and the image combiner 149 combines the color-mapped substance images while applying the brightness information obtained by the brightness information obtainer 141. In other words, a color channel mapped to a substance image is combined with a brightness channel mapped to the brightness information. In the meantime, color mapping may be performed with constant saturation or different saturation for each substance image. Although in the aforementioned exemplary embodiments, a color space where brightness information and color information are separated is employed, another color space where the color information contains the brightness information may be used in other exemplary embodiments.

The CMY color space, CMYK color space, and RGB color space are all the color space where the color information includes the brightness information. For example, if the RGB color space is employed, the color mapper 148 may map the red and blue channels to the separated two substance images, respectively, and the image combiner 149 may map the green channel that may look brightest to the brightness image, and combine the green channel with the red and blue channels. If the CMYK color space is employed, two or three of Cyan, Magenta, Yellow, and Black channels are mapped to the respective substance images and the remaining channel is mapped to the brightness image. The mapped channels may then be combined.

Because the region of interest in the subject area includes an object of interest to be constantly watched by the user during an X-ray scan, obtaining a high resolution image takes priority even if a dose of X-ray to be irradiated to the region of interest rather increases. On the contrary, because the background region in the subject area does not include the object of interest, reducing the exposure of the subject to X-radiation takes priority over obtaining a high resolution image with an increased dose of X-rays, even if a rather low resolution image may be obtained. In the following embodiment, an X-ray imaging apparatus is provided. The X-ray imaging apparatus obtains a high resolution image of a region of interest by increasing a dose of X-rays to be irradiated to the region of interest, and obtains an image of the background region with a good SNR using the low-dose image restoration scheme as described in the aforementioned exemplary embodiment even if a lower dose of X-rays are irradiated to the background region. The X-ray imaging apparatus in accordance with another exemplary embodiment will now be described in detail.

Figure 12:
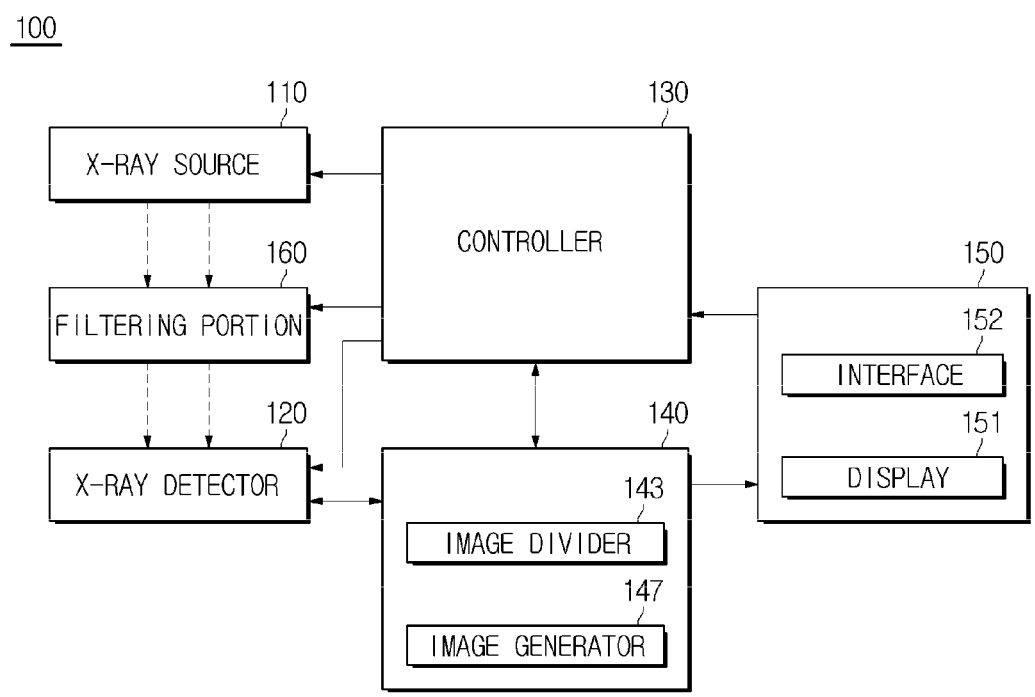
FIG. 12 is a control block diagram of an X-ray imaging apparatus, according to another exemplary embodiment.
Figure 13:
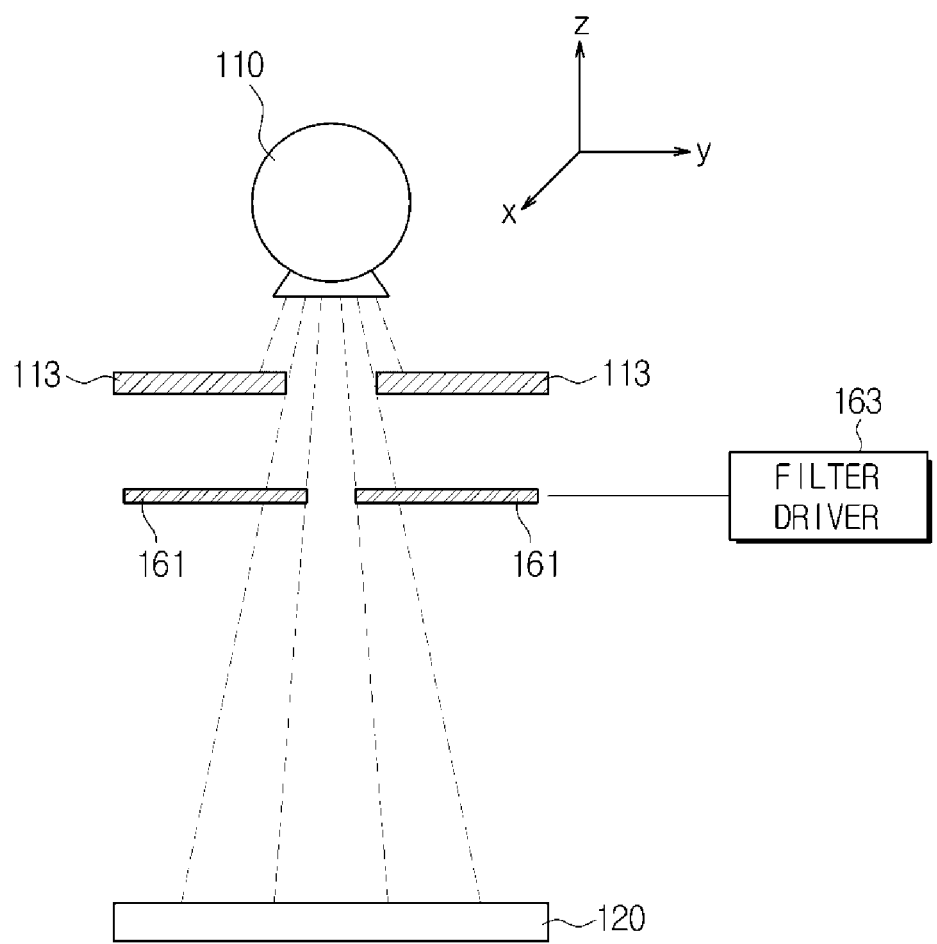
FIG. 13 is a side cross-sectional view of a region-of-interest filter included in a filtering portion of FIG. 12.
Figure 14:
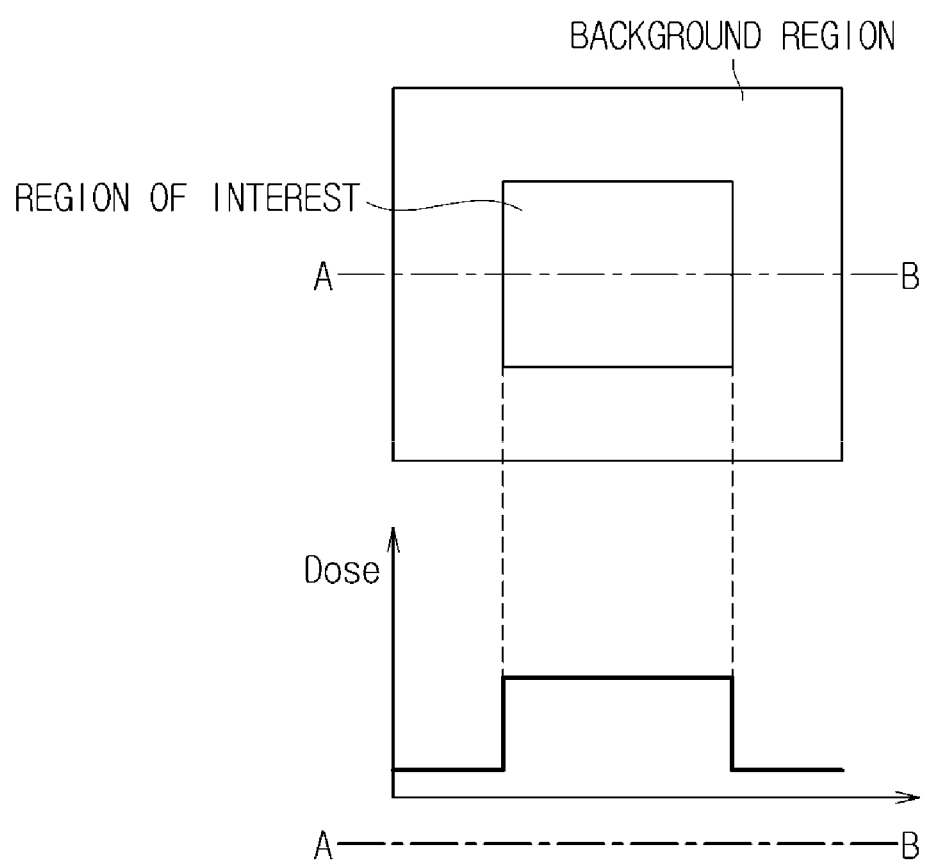
FIG. 14 is a diagram illustrating X-ray irradiation doses in a region of interest and a background region of FIG. 12.

FIG. 12 is a control block diagram of an X-ray imaging apparatus, according to another exemplary embodiment, FIG. 13 is a side cross-sectional view of a region-of-interest filter included in a filtering portion of FIG. 12, and FIG. 14 is a diagram illustrating X-ray irradiation doses in a region of interest and a background region of FIG. 12.

Referring to FIG. 12, the X-ray imaging apparatus 100 includes the X-ray source 110 for generating and irradiating X-rays, the X-ray detector 120 for detecting irradiated X-rays to obtain frame images, and a filtering portion 160 for filtering X-rays irradiated to the background region. The X-ray imaging apparatus 100 further includes the controller 130 for controlling operation of the X-ray source 110, X-ray detector 120, and the filtering portion 160, the image processor 140 for performing image processing on the frame images obtained by the X-ray detector 120, and the user interface 150 for providing information to the user and receiving control commands from the user. Description of the same components as described in the aforementioned exemplary embodiment will be omitted herein.

The filtering portion 160 may filter the X-rays from the X-ray source 110 such that a lower dose of X-rays are irradiated to the background region than those irradiated to the region of interest. This is to reduce exposure of the subject to radiation by applying a rather higher dose of X-rays to the region of interest that has more information about the inside of the subject while applying a lower dose of X-rays to the background region that is less informative.

Referring to FIG. 13, the filtering portion 160 includes a region-of-interest filter 161 and a filter driver 163 for moving the region-of-interest filter 161. The filter driver 163 may include a motor to generate a moving force, and a mechanical structure, such as a gear to deliver the moving force to the region-of-interest filter 161. The region-of-interest filter 161 may be moved by the filter driver 163 in the three dimensional (3D) space defined by x, y, and z-axes. It may be moved on the xy-plane or along the z-axis. Movement on the xy-plane is to corresponding locations of the region-of-interest filter 161 and the background region, and movement along the z-axis is to correspond to the sizes of the region-of-interest filter 161 and the region of interest.

The filter portion 160 further includes a collimator 113 arranged in front of the X-ray source 110 in the direction of X-ray irradiation. The collimator 113 may be made of a material, such as lead, or tungsten that absorbs or cuts off X-rays, to adjust the range of FOV, which is an area to which the X-ray source 110 irradiates X-rays, and reduce X-ray scattering. The region-of-interest filter 161 is located between the collimator 113 and the X-ray detector 120 for filtering X-rays incident to the X-ray detector 120. As the region-of-interest filter 161 is made of a material that attenuates X-rays, the X-rays attenuate while passing through the region-of-interest filter 161, and the X-ray dose decreases. Accordingly, locating the region-of-interest filter 161 in a position that corresponds to the background region of the subject area may allow a lower dose of X-rays to be incident to the background region than an X-ray dose to the region-of interest. Because the region of interest is surrounded by the background region, the region-of-interest filter 161 may have a form with a cavity in the center, e.g., a ring form with an opening in the center.

The image processor may detect an object of interest from a frame image obtained by the X-ray detector 120, and set up an area that contains the object of interest as the region of interest. The object of interest is an object that has constant attention during X-ray scanning, such as a treatment instrument used for the subject, or a region for treatment or a part of lesions. The controller may generate a control signal to move the region-of-interest filter 161 based on information obtained from the image processor about the region of interest, send the control signal to the filter driver 163 to move the region-of-interest filter 161 to a position that corresponds to the background region. Once the region-of-interest filter 161 is moved to the position that corresponds to the background region, X-rays incident to the background region is filtered by the region-of-interest filter 161, and the X-rays that pass through the opening of the region-of-interest filter 161 are incident to the region of interest. If the X-ray source 110 irradiates X-rays in a fan beam form or cone beam form, the nearer the region-of-interest filter 161 is moved to the X-ray source 110 or the collimator 113, the narrower the width of the X-rays to be incident upon the region-of-interest filter 161 is, and in the opposite case, the width of X-rays incident on the region-of-interest filter 161 gets wider. The wider the width of the X-rays incident on the region-of-interest filter 161 is, the wider the filtering region is. Accordingly, to increase the region of interest by decreasing the filtering region, the region-of-interest filter 161 is moved toward the X-ray source 110 or the collimator 113 along the z-axis, or to decrease the region of interest by increasing the filtering region, the region-of-interest filter 161 is moved in the opposite direction of the X-ray source 110 or the collimator 113 along the z-axis.

In the meantime, the image processor may obtain information about image characteristics of a frame image as well as information about the region of interest and forward the information to the controller, which may in turn control the X-ray source 110 and the filtering portion based on the information. The controller may control a X-ray dose per frame based on the noise level in the region of interest, using the tube current and the exposure time. For example, if the noise level in the region of interest is higher than a predetermined threshold, the X-ray dose per frame may be controlled to increase to decrease the noise level, and if the noise level in the region of interest is lower than the predetermined threshold, the X-ray dose per frame may be controlled to decrease to reduce exposure of the subject to radiation.

Furthermore, the controller may determine a difference in X-ray dose incident onto the region of interest and background region based on image characteristics of the region of interest and background region, such as noise, motion, contrast, or the like, and control a dose of X-rays to be incident onto the background region according to the determined difference in X-ray dose. For this, the filtering portion may include multiple region-of-interest filters having different X-ray attenuation, and the controller may control a dose of X-rays to be incident onto the background region by changing the region-of-interest filters or selectively combining the multiple region-of-interest filters. Such a region-of-interest filter is, however, only an example to be employed, but other various types of filters may be employed to reduce a dose of X-rays to be incident onto the background region.

FIG. 14 shows X-ray doses incident on straight line AB that passes through the region of interest and background region. When the controller moves the region-of-interest filter to a position that corresponds to the background region, a lower dose of X-rays are incident onto the background region than that onto the region of interest, as shown in FIG. 14. As the lower dose of X-rays is incident onto the background region, exposure of the subject to the X-radiation may be reduced. The lower dose of X-rays incident onto the background region might drop an SNR of the frame image, but the SNR of the frame image may increase according to the low-dose image restoration scheme as described in the aforementioned exemplary embodiment.

The image divider may perform substance separation on the multiple frame images of the background region input from the X-ray detector and apply the low-dose image restoration scheme, but may not do the same for the multiple frame images of the region of interest. In the present embodiment, a relatively high dose of X-rays are irradiated to the region of interest, and thus, unlike the aforementioned exemplary embodiment, the image divider may not perform substance separation for low-dose image restoration on the frame images of the region of interest. However, in the present embodiment, there is an occasion where multiple substance images may be separated from a frame image of the region of interest for the color mapping. Accordingly, separation of the substance images for the region of interest may be selectively performed.

When the X-ray detector generates and sends a frame image of the region of interest to the image generator, the image generator may perform high resolution image restoration on the frame image of the region of interest.

Because the region of interest is a region to be carefully watched for diagnosis or treatment on the subject, the motion is carefully captured, and the frame image is represented in higher resolution to a point where even tiny objects are seen better. As an example of representing a frame image of the region of interest in higher resolution, a high resolution image restoration scheme may be employed to combine multiple frame images into a high resolution image. The image generator may perform image restoration each time a predetermined number of images are received. For example, it may perform image restoration each time 6 frame images are received. The image generator waits until 6 frame images are input, matching them to restore a high resolution frame image once the 6 frame images are input. It may wait for another 6 frame images to be input, and then restore a high resolution frame image from the 6 frame images. Alternatively, the image generator may perform image restoration while shifting the frame images one by one, using the sliding window method, instead of waiting for six frame images to be input. There are no limitations on the number of frame images used in the image restoration, although six frame images are used to restore the frame image with a good SNR.

The image generator may restore a high resolution image from frame images of the region of interest through image interpolation that inserts a pixel having a proper value between the existing pixels of the frame images. For this, various high resolution image restoration schemes may be employed, including a scheme for restoring a high resolution image by analyzing relations between low and high resolution images in the frequency domain, a scheme for applying Projections Onto Convex Set (POCS), a Maximum A Posteriori (MAP) estimation based scheme, a hybrid scheme into which the MAP estimation based scheme and the scheme for applying POCS are integrated, etc.

Furthermore, the image generator may perform motion estimation in a sub-pixel accuracy unit in matching multiple consecutive frame images.

As a motion estimation scheme, there may be a scheme for obtaining correlation spectrum in the frequency domain through Discrete Fourier Transform (DFT) between images, and a scheme for extracting motion information in the sub-pixel accuracy unit by investigating sub pixels of the original image.

The restored high resolution frame image of the region of interest may be combined with a frame image of the background region into the whole image that represents the subject area, and the whole image may then be displayed on the display.

To restore the frame image of the background image, the X-ray detector may input respective X-ray data for the multiple energy bands, e.g., three energy bands $E_{band1}$, $E_{band2}$, $E_{band3}$ for each frame, to the image divider. In other words, the frame image of the background region obtained by the X-ray detector at a frame rate, and input to the image divider may include multiple pieces of X-ray data that correspond to the multiple energy bands.

The image divider may separate substance images from the multiple frame images of the background region input from the X-ray detector. How to separate the substance images is the same as what is described in the aforementioned exemplary embodiment, so the description will be omitted herein.

As shown in FIG. 6, after the image divider 143 divides each of the multiple frame images into different substance images, the image generator may obtain a frame image with an increased SNR by performing motion estimation and compensation on the separated substance images. As shown in FIG. 7, the image generator 147 may increase the SNR by combining images that represent the same substance among the multiple substance images separated from the respective frame images. For example, the image generator 147 may restore a bones image with an increased SNR in the current frame, by combining the bones image of the current frame bn with the same bones images of previous frames bn−2, bn−1, . . . . As for organs or blood vessels, their images may be restored with increased SNRs in the same way. How to combine a substance image of the current frame with the substance image of the previous frames is the same as what is described in the aforementioned exemplary embodiment, so the description will be omitted herein.

As described above, SNR may be improved by combining a substance image of the current frame and substance images of the previous frames, but if there is a motion of the subject between frames, image blurring may occur. As for the X-ray imaging apparatus in accordance with the exemplary embodiments of the present disclosure, because the X-ray imaging apparatus irradiates a low dose of X-rays, image blurring may be conspicuous due to the motion of a subject if many frames are used for image matching. In an exemplary embodiment, to reduce image blurring that may occur when a substance image of the current frame is combined with the substance image of the previous frames, additional image enhancement, such as motion estimation and compensation may be performed. Description of this is the same as in the aforementioned exemplary embodiment, and thus omitted herein.

The image generator may restore a substance image having a good SNR by combining a substance image of the current frame with the same substance images of the previous frames, and in the restoration process, motion estimation and compensation may be applied to avoid image blurring due to motion of the subject. The image generator may finally restore the current frame image by combining respective substance images in the current frame with enhanced SNR and image blurring. Even though the restored frame image of the background region is obtained through low dose X-ray irradiation, it may have an excellent SNR and resolution.

Moreover, the image processor may additionally perform an image equalization algorithm to match the brightness and contrast between the frame images of the region of interest and background region.

Where a frame image is obtained by irradiating relatively high dose of X-rays to the region of interest while irradiating lower dose of X-rays to the background region, not only the frame image of the region of interest but also the frame of the background region in the frame may have high resolution, and exposure of the subject to the X-radiation may be reduced.

Figure 15:
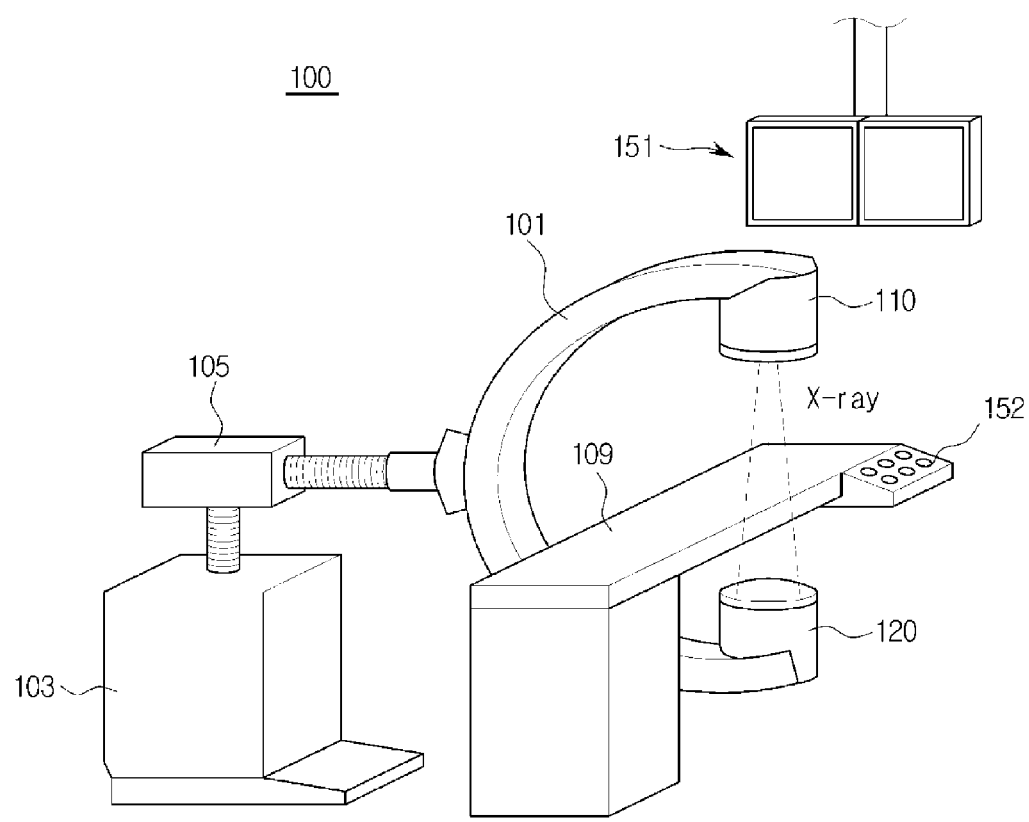
FIG. 15 is an exterior view of an X-ray imaging apparatus, according to an exemplary embodiment.

FIG. 15 is an exterior view of an X-ray imaging apparatus, according to an exemplary embodiment.

For example, the X-ray imaging apparatus 100 includes a C-arm 101 as shown in FIG. 15. The X-ray source 110 and the X-ray detector 120 may be mounted at either end of the C-arm 101. The C-arm 101 is connected to a main body 103 via a connecting shaft 105, and rotated in the orbital direction.

An X-ray tube, a collimator, and a filtering portion may be included in the X-ray source 110. A subject table 109 is placed between the X-ray source 110 and the X-ray detector 120. The subject may lie on the subject table 109, and the X-ray source 110 irradiates X-rays to the subject on the subject table 109. The X-ray detector 120 detects X-rays that penetrate the subject, and obtains an X-ray image of the subject.

As described above, the X-ray imaging apparatus 100 may obtain a video clip about the subject in real time, in which case the user may perform treatment or diagnosis while looking at the display 151 that may present various images used for the treatment or diagnosis.

The user may select whether to use a low-dose image restoration scheme through an input interface 152 in accordance with the aforementioned exemplary embodiment. In other words, the user may freely determine whether to select the low-dose image restoration scheme according to the portions or purposes of examination. Once the low-dose image restoration scheme is selected through the input interface 152, the controller may control the image processor to perform the low-dose image restoration scheme. Alternatively, the input interface 152 may directly send a command to perform the low-dose image restoration scheme to the image processor.

As described above, the low-dose image restoration scheme may be selected by the user, or automatically determined based on the portions to be examined or their motion properties. Because it is difficult to make elaborate motion estimation with an image processing algorithm if the subject makes a large motion, the controller determines whether it is possible to effectively apply the low-dose image restoration scheme for the portion to be examined, based on the information about the portion to be examined or its motion properties.

Furthermore, in applying the low-dose image restoration scheme, determinations according to both analysis from the controller and the user's selection may be taken into account. For example, if it is determined from the analysis performed by the controller that applying the low-dose image restoration scheme would not be effective, before or after the low-dose image restoration scheme is selected by the user, a message including the analysis result may be presented for the user to reconsider the determination about selecting the low-dose image restoration scheme.

The X-ray imaging apparatus 100 able to provide X-ray video clips provides a low-dose mode, and may set a rule that the low-dose image restoration scheme is performed only when the low-dose mode is selected through the input interface 152.

Figure 16:
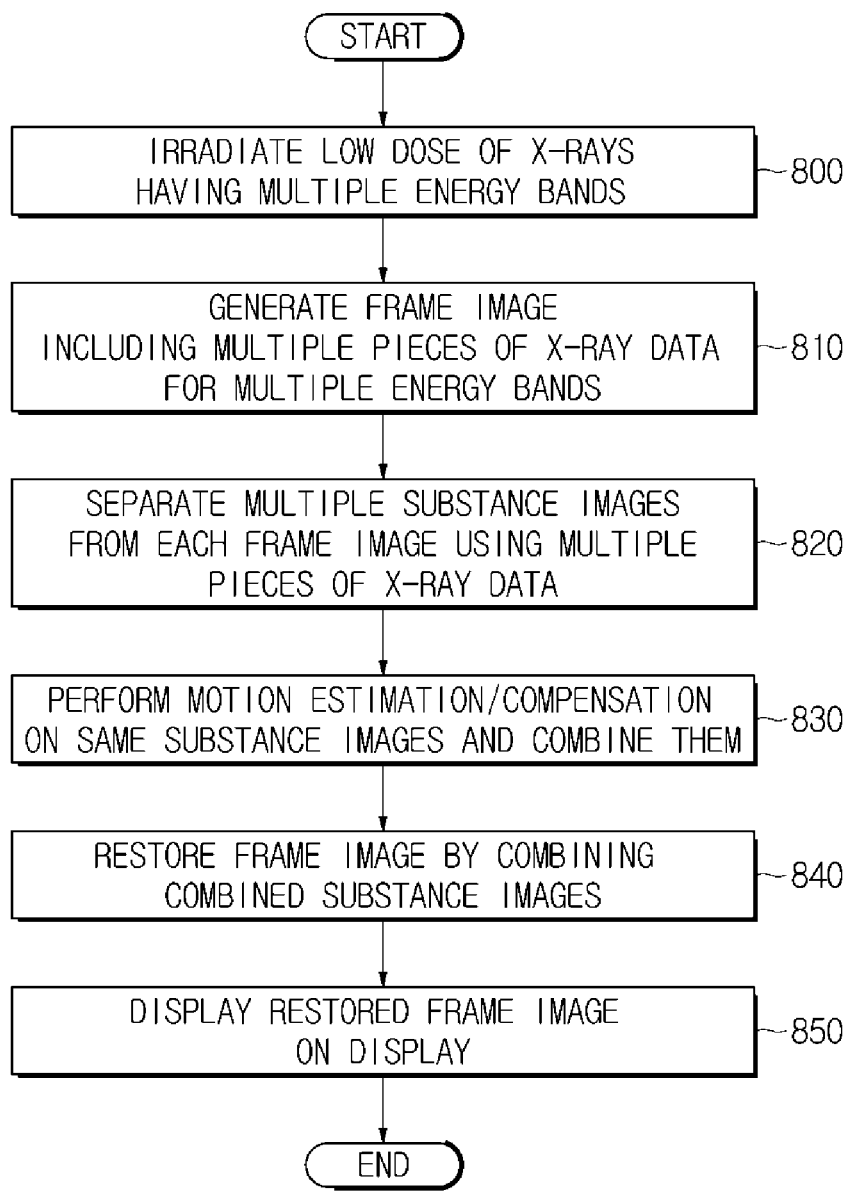
FIG. 16 is a flowchart illustrating a method for generating X-ray images, according to an exemplary embodiment.

FIG. 16 is a flowchart illustrating a method for generating X-ray images, according to an exemplary embodiment.

Referring to FIG. 16, in operation 800, an X-ray source irradiates a low dose of X-rays having multiple energy bands to a subject. In operation 810, an X-ray detector detects X-rays penetrating the subject, and generates a frame image including multiple pieces of X-ray data for the multiple energy bands, respectively.

As described above, as a way of obtaining pieces of X-ray data for different energy bands, there are a method for irradiating X-rays multiple times while varying the energy band, by the X-ray source, and a method for irradiating a wide band of X-rays at once, by the X-ray source, and detecting and dividing them into different energy bands, by the X-ray detector. If the former method is employed by the X-ray imaging apparatus, the X-ray source irradiates X-rays of an energy band $E_{band1}$, and the X-ray detector detects them to obtain an X-ray image for the energy band $E_{band1}$. In the same method, X-ray images for energy bands $E_{band2}$ and $E_{band3}$ are obtained as well. If the latter method is employed by the X-ray imaging apparatus, the X-ray source irradiates a wide band of X-rays at once, including three energy bands, as shown in FIG. 4B, and the X-ray detector detects and divides the X-rays into the respective energy bands. The detailed description will be omitted herein.

As described above, the X-ray detector may input the respective X-ray data for the multiple energy bands, e.g., the three energy bands $E_{band1}$, $E_{band2}$, $E_{band3}$, for each frame to the image divider.

In operation 820, the X-ray detector inputs the frame image including the multiple pieces of X-ray data for the multiple energy bands to the image divider, the image divider divides the frame image into multiple substance images, or separates the multiple substance images from each frame image, using the multiple pieces of X-ray data.

If two types of substances is to be separated, the image divider may separate images of the two substances from a frame image by performing two-stage operations: applying a weight to at least one of two pieces of X-ray data corresponding to two energy bands included in the frame image; and performing subtraction. In another example, if there are three or more types of substances for separation, the image divider may separate images of the three or more types of substances from a frame image by applying proper weights to respective pieces of X-ray data that correspond to three or more energy bands of the frame image, and subtracting them. For example, the image divider may divide each frame image into three substances, such as bones, soft tissues, and blood vessels having different motion properties, thereby generating multiple substance images.

In operation 830, an image generator performs motion estimation/compensation on the same substance images, and combines the same substance images. In operation 840, the image generator restores a frame image by combining the combined substance images. In operation 850, the image generator displays the restored frame image on a display.

Figure 17:
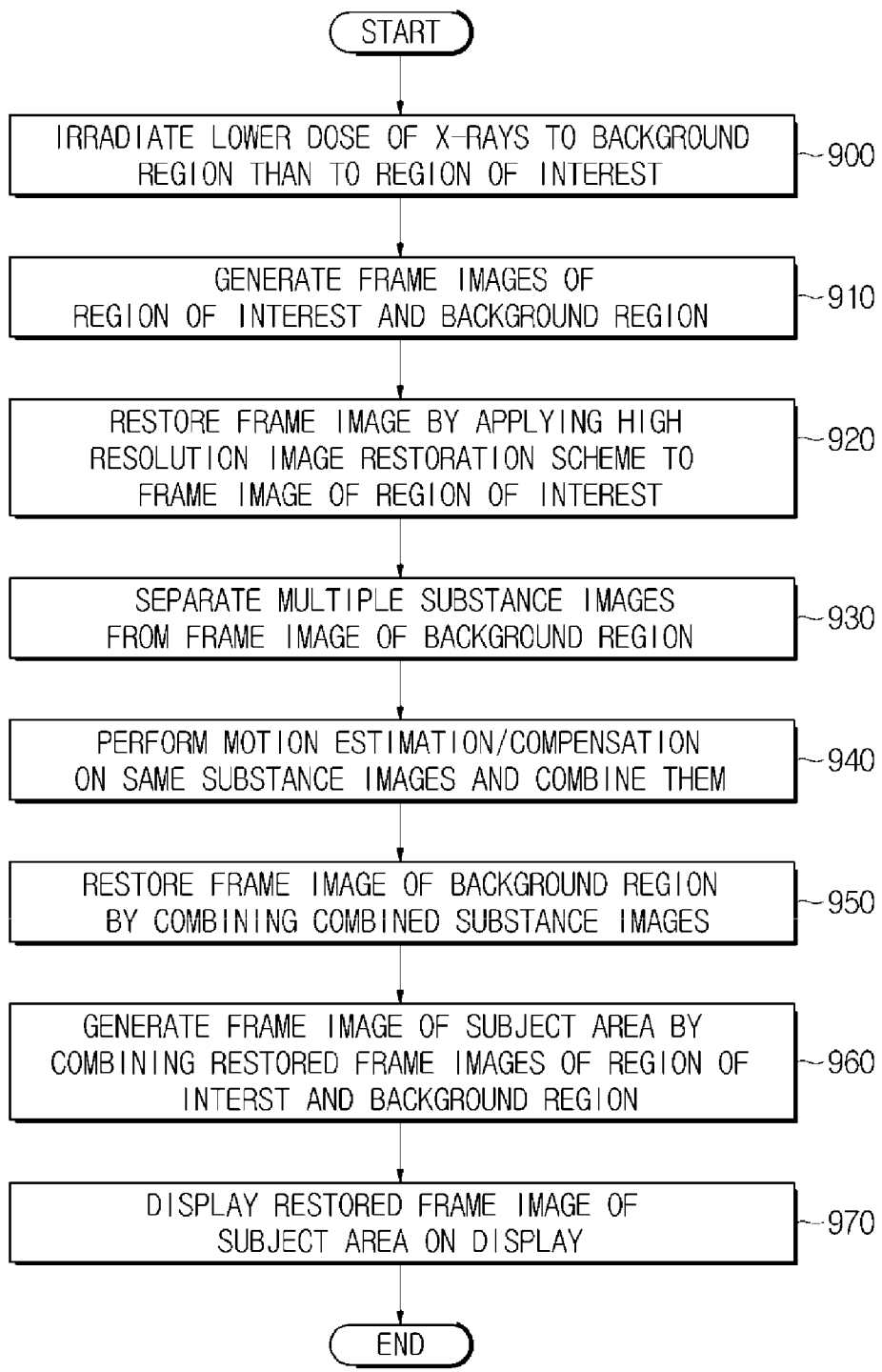
FIG. 17 is a flowchart illustrating a method for generating X-ray images, according to another exemplary embodiment.

FIG. 17 is a flowchart illustrating a method for generating X-ray images, according to another exemplary embodiment.

Referring to FIG. 17, in operation 900, a filtering portion filters X-rays irradiated from an X-ray source to irradiate a lower dose of X-rays to a background region than that to a region of interest of a subject. In operation 910, an X-ray detector detects X-rays penetrating the subject, and generates frame images of the region of interest and background region.

In operation 920, an image generator restores the frame image of the region of interest by applying a high resolution image restoration scheme to the frame image of the region of interest. In operation 930, an image divider divides the frame image of the background region into multiple substance images, or separates the multiple substance images from the frame image of the background region.

In operation 940, the image generator performs motion estimation/compensation on the same substance images, and combines the same substance images. In operation 950, the image generator restores the frame image of the background region by combining the combined substance images.

In operation 960, the image generator generates a frame image of a subject area by combining the restored frame images of the region of interest and background region. In operation 970, the image generator displays the generated or restored frame image of the subject area on a display.

That is, the image generator generates a whole image that represents the subject area by combining the restored frame images of the region of interest and background region, and the display displays the whole image of the subject area. The image processor may additionally perform an image equalization algorithm to match brightness and contrast between the frame images of the region of interest and background region. Where a frame image is obtained by irradiating a relatively high dose of X-rays to the region of interest while irradiating a lower dose of X-rays to the background region, not only the frame image of the region of interest but also the frame of the background region in the frame may have high resolution, and exposure of the subject to the X-rays may be reduced.

According to the exemplary embodiments of the present disclosure, the X-ray imaging apparatus and the method for generating X-ray images may help reduce the patient's exposure to X-ray radiation, and obtain high resolution images.

The foregoing exemplary embodiments and advantages are examples and are not to be construed as limiting. The present teaching may be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An X-ray imaging apparatus comprising:
   an X-ray source configured to irradiate X-rays to a subject;
   an X-ray detector configured to detect X-rays penetrating the subject, and generate a pieces of X-ray data for energy bands to produce a frame image;
   an image processor configured to divide the frame image into images of substances, using the pieces of the X-ray data and
   restore the frame image by performing motion compensation on an image of a first substance of the frame image, among the images of the substances of the frame image, and an image of the first substance of a previous frame image.

2. The X-ray imaging apparatus of claim 1, wherein the image processor is configured to restore the frame image by combining the motion-compensated images of the first substance, and combining the combined images of the first substance with images of a second substance that are combined among the substances.

3. The X-ray imaging apparatus of claim 1, wherein the image processor is configured to perform motion estimation and motion compensation on the image of the first substance of the frame image and the image of the first substance of the previous frame image.

4. The X-ray imaging apparatus of claim 1, wherein the image processor is configured to separate the images of the substances from the pieces of the X-ray data, using a difference in an attenuation property between the substances.

5. The X-ray imaging apparatus of claim 1, wherein the X-ray source is configured to irradiate X-rays having the energy bands to the subject.

6. The X-ray imaging apparatus of claim 1, wherein the X-ray source is configured to irradiate X-rays having each of the energy bands to the subject.

7. The X-ray imaging apparatus of claim 1, wherein the X-ray source is further configured to vary energy bands of the irradiated X-rays by changing at least one among a tube voltage and a filter.

8. The X-ray imaging apparatus of claim 1, further comprising a filtering portion configured to filter the irradiated X-rays such that a dose of the X-rays irradiated to a background region of the subject is lower than a dose of the X-rays irradiated to a region of interest of the subject.

9. The X-ray imaging apparatus of claim 8, wherein the X-ray detector is configured to:
   detect X-rays penetrating the background region;
   generate a frame image of the background region comprising pieces of X-ray data of the background region for multiple energy bands;
   detect X-rays penetrating the region of interest; and
   generate a frame image of the region of interest.

10. The X-ray imaging apparatus of claim 9, wherein the image processor is configured to divide the frame image of the background region into images of substances, using the pieces of the X-ray data of the background region, and
   restore the frame image of the background region by performing motion compensation on an image of the first substance of the frame image of the background region, among the images of the substances of the frame image of the background region, and an image of the first substance of a previous frame image of the background region, and restore the frame image of the region of interest by performing high resolution image restoration on the frame image of the region of interest.

11. The X-ray imaging apparatus of claim 10, wherein the image processor is configured to combine the restored frame images of the background region and the region of interest into a frame image of the subject.

12. The X-ray imaging apparatus of claim 1, further comprising a color mapper configured to map different color channels to the images of the substances.

13. An X-ray imaging apparatus comprising:
   an image divider configured to divide a frame image comprising pieces of X-ray data for energy bands, into images of substances; and
   an image generator configured to restore the frame image by performing motion compensation on an image of a first substance of the frame image, among the images of the substances of the frame image, and an image of the first substance of a previous frame image.

14. The X-ray imaging apparatus of claim 13, wherein the image generator is configured to restore the frame image by combining the motion-compensated images of the first substance, and combining the combined images of the first substance with images of a second substance that are combined among the substances.

15. The X-ray imaging apparatus of claim 13, wherein the image generator is configured to perform motion estimation and motion compensation on the image of the first substance of the frame image and the image of the first substance of the previous frame image.

16. The X-ray imaging apparatus of claim 13, wherein the image divider is configured to separate the images of the substances from the pieces of the X-ray data, using a difference in an attenuation property between the substances.

17. The X-ray imaging apparatus of claim 13, wherein the image divider is configured to divide a frame image of a background region of a subject into images of substances, and
the image generator is configured to restore the frame image of the background region by performing motion compensation on an image of the first substance of the frame image of the background region, among the images of the substances of the frame image of the background region, and an image of the first substance of a previous frame image of the background region, and restore a frame image of a region of interest of the subject by performing high resolution image restoration on the frame image of the region of interest.

18. The X-ray imaging apparatus of claim 17, wherein the image generator is configured to combine the restored frame images of the background region and the region of interest into a frame image of the subject.

19. A method of generating X-ray images, the method comprising:
irradiating X-rays to a subject;
detecting X-rays penetrating the subject;
generating a frame image comprising pieces of X-ray data for energy bands;
dividing the frame image into images of substances, using the pieces of the X-ray data; and
restoring the frame image by performing motion compensation on an image of a first substance of the frame image, among the images of the substances of the frame image, and an image of the first substance of a previous frame image.

20. The method of claim 19, wherein the restoring comprises:
combining the motion-compensated images of the first substance; and
combining the combined images of the first substance with images of a second substance that are combined among the substances.

21. The method of claim 19, wherein the restoring comprises performing motion estimation and motion compensation on the image of the first substance of the frame image and the image of the first substance of the previous frame image.

22. The method of claim 19, wherein the dividing comprises separating the images of the substances from the pieces of the X-ray data, using a difference in an attenuation property between the substances.

23. The method of claim 19, wherein the irradiating comprises irradiating X-rays having the energy bands to the subject.

24. The method of claim 19, wherein the irradiating comprises irradiating X-rays having each of the energy bands to the subject.

25. The method of claim 19, wherein the generating comprises:
detecting X-rays penetrating a background region of the subject;
generating a frame image of the background region comprising pieces of X-ray data of the background region for multiple energy bands;
detecting X-rays penetrating a region of interest of the subject; and
generating a frame image of the region of interest.

26. The method of claim 25, wherein the dividing comprises dividing the frame image of the background region into images of substances, using the pieces of the X-ray data of the background region, and
the restoring comprises restoring the frame image of the background region by performing motion compensation on an image of the first substance of the frame image of the background region, among the images of the substances of the frame image of the background region, and an image of the first substance of a previous frame image of the background region, and restoring the frame image of the region of interest by performing high resolution image restoration on the frame image of the region of interest.

27. The method of claim 26, wherein the restoring comprises combining the restored frame images of the background region and the region of interest into a frame image of the subject.

28. The method of claim 19, further comprising determining whether an X-ray imaging apparatus is operating in a low dose mode,
wherein the generating comprises generating the frame image comprising the pieces of the X-ray data for the energy bands, in response to the determining that the X-ray imaging apparatus is operating in the low dose mode.

29. The method of claim 19, further comprising determining whether a mode to restore a frame image through separation of images of substances is selected,
wherein the generating comprises generating the frame image comprising the pieces of the X-ray data for the energy bands, in response to the determining that the mode to restore a frame image is selected.

* * * * *